US012779229B2

(12) United States Patent
Wheeler et al.

(10) Patent No.: US 12,779,229 B2
(45) Date of Patent: Nov. 3, 2026

(54) IMPLANTABLE INTRA- AND TRANS-BODY WIRELESS NETWORKS FOR THERAPIES

(71) Applicant: THE CHARLES STARK DRAPER LABORATORY, INC., Cambridge, MA (US)

(72) Inventors: Jesse J. Wheeler, Cambridge, MA (US); Jake G. Hellman, Watertown, MA (US); Carlos A. Segura, Ipswich, MA (US); John R. Burns, IV, Boston, MA (US); Alejandro J. Miranda, Winthrop, MA (US); Elliot H. Greenwald, Cambridge, MA (US); Andrew Czarnecki, Quincy, MA (US); Matthew C. Muresan, Somerville, MA (US); Wes T. Uy, Quincy, MA (US); Caroline K. Bjune, Arlington, MA (US); John Roland Lachapelle, Princeton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 1074 days.

(21) Appl. No.: 17/095,364

(22) Filed: Nov. 11, 2020

(65) Prior Publication Data

US 2021/0069518 A1 Mar. 11, 2021

Related U.S. Application Data

(62) Division of application No. 16/189,862, filed on Nov. 13, 2018, now abandoned.

(Continued)

(51) Int. Cl.
*A61N 1/372* (2006.01)
*A61B 5/24* (2021.01)
(Continued)

(52) U.S. Cl.
CPC ............ *A61N 1/37217* (2013.01); *A61B 5/24* (2021.01); *A61N 1/0534* (2013.01);
(Continued)

(58) Field of Classification Search
CPC ............ A61N 1/37217; A61N 1/37288; A61N 1/37211; A61N 1/0534; A61N 1/36125;
(Continued)

(56) References Cited

U.S. PATENT DOCUMENTS 4,088,138 A * 5/1978 Diack ...................... A61B 5/25 600/513
4,202,342 A * 5/1980 Keller, Jr. .......... A61N 1/37211 607/30

(Continued)

OTHER PUBLICATIONS

International Search Report and Written Opinion from International Application No. PCT/US2018/060832 dated Feb. 5, 2019.

*Primary Examiner* — Eugene T Wu
(74) *Attorney, Agent, or Firm* — Brooks Kushman, P.C.

(57) ABSTRACT

A system of two or more implantable medical devices is configured to establish an intra-body wireless communication link between the two or more implantable medical devices while the two or more implantable medical devices are implanted in a body of a patient, and to coordinate therapy for the patient through the communication link between the two or more implantable medical devices.

30 Claims, 23 Drawing Sheets

Related U.S. Application Data

(60) Provisional application No. 62/585,346, filed on Nov. 13, 2017.

(51) Int. Cl.

| | |
|---|---|
| ***A61N 1/05*** | (2006.01) |
| ***A61N 1/36*** | (2006.01) |
| ***A61N 1/378*** | (2006.01) |
| *A61B 5/00* | (2006.01) |
| *A61N 1/375* | (2006.01) |

(52) U.S. Cl.

CPC ...... *A61N 1/36125* (2013.01); *A61N 1/37211* (2013.01); *A61N 1/37288* (2013.01); *A61N 1/3787* (2013.01); *A61B 5/0031* (2013.01); *A61B 2560/045* (2013.01); *A61N 1/0531* (2013.01); *A61N 1/36064* (2013.01); *A61N 1/37252* (2013.01); *A61N 1/3758* (2013.01)

(58) Field of Classification Search

CPC ................ A61N 1/3787; A61N 1/0531; A61N 1/36064; A61N 1/37252; A61N 1/3758; A61B 5/24; A61B 5/291; A61B 5/0031; A61B 2560/045

See application file for complete search history.

(56) References Cited

U.S. PATENT DOCUMENTS

| | | | | | |
|---|---|---|---|---|---|
| 4,592,359 | A * | 6/1986 | Galbraith | A61N 1/36038 | 607/57 |
| 4,768,511 | A * | 9/1988 | DeCote, Jr. | A61N 1/365 | 607/9 |
| 5,243,977 | A * | 9/1993 | Trabucco | A61N 1/0587 | 607/129 |
| 5,370,672 | A * | 12/1994 | Fowler | A61N 1/32 | 607/58 |
| 5,450,845 | A * | 9/1995 | Axelgaard | A61B 5/27 | 600/382 |
| 5,758,651 | A * | 6/1998 | Nygard | A61N 1/36038 | 607/57 |
| 6,035,237 | A * | 3/2000 | Schulman | A61N 1/36142 | 607/57 |
| 6,038,480 | A * | 3/2000 | Hrdlicka | A61N 1/0551 | 607/116 |
| 6,358,202 | B1 * | 3/2002 | Arent | G16H 40/63 | 600/300 |
| 7,257,439 | B2 * | 8/2007 | Llinas | G06F 3/015 | 606/32 |
| 8,594,802 | B2 | 11/2013 | Stahmann et al. | | |
| 2002/0123673 | A1 * | 9/2002 | Webb | A61B 5/0031 | 607/31 |
| 2003/0041866 | A1 * | 3/2003 | Linberg | A61N 1/37264 | 128/899 |
| 2004/0088027 | A1 * | 5/2004 | Burnes | G16H 10/60 | 607/60 |
| 2005/0187594 | A1 | 8/2005 | Hatlestad | | |
| 2005/0222631 | A1 | 10/2005 | Dalal et al. | | |
| 2006/0052833 | A1 * | 3/2006 | Legay | A61N 1/3706 | 607/27 |
| 2007/0067003 | A1 | 3/2007 | Sanchez et al. | | |
| 2008/0046037 | A1 * | 2/2008 | Haubrich | A61N 1/37211 | 607/60 |
| 2008/0046038 | A1 * | 2/2008 | Hill | A61M 5/14276 | 607/60 |
| 2008/0129465 | A1 * | 6/2008 | Rao | A61N 1/37 | 340/286.02 |
| 2009/0201148 | A1 | 8/2009 | Tran et al. | | |
| 2010/0228314 | A1 | 9/2010 | Goetz | | |
| 2011/0196451 | A1 * | 8/2011 | Hill | G16H 50/20 | 607/60 |
| 2013/0012802 | A1 | 1/2013 | Horseman | | |
| 2014/0094674 | A1 * | 4/2014 | Nurmikko | A61N 1/37229 | 600/378 |
| 2014/0275849 | A1 * | 9/2014 | Acquista | A61B 5/0024 | 600/301 |
| 2015/0065047 | A1 | 3/2015 | Wu et al. | | |
| 2016/0206892 | A1 | 7/2016 | Demmer | | |
| 2016/0330573 | A1 * | 11/2016 | Masoud | G06F 21/606 | |
| 2016/0331973 | A1 * | 11/2016 | Wheeler | H04L 43/16 | |
| 2017/0161449 | A1 | 6/2017 | Meskens | | |
| 2017/0196457 | A1 | 7/2017 | Thakur et al. | | |
| 2017/0223540 | A1 | 8/2017 | Battiwalla et al. | | |
| 2018/0027077 | A1 * | 1/2018 | Melodia | H04W 4/38 | 370/254 |
| 2019/0111267 | A1 | 4/2019 | Chatalic et al. | | |
| 2019/0143126 | A1 | 5/2019 | Wheeler et al. | | |

* cited by examiner

810

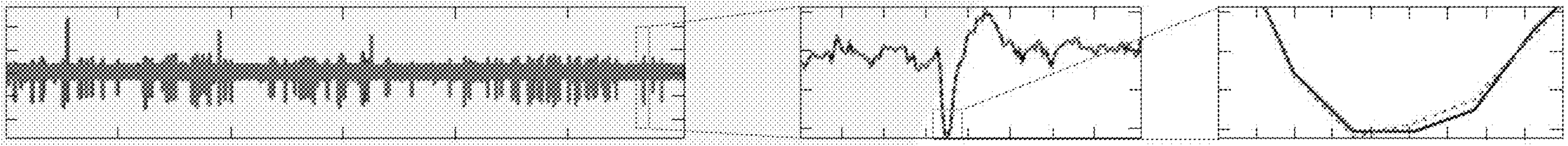

| Signal Range Max | Min | | Original (16-bit) 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|---|---|
| 32768 | 16384 | 1 | 0 | 1 | a | b | c | X | X | X | X | X | X | X | X | X | X | X |
| 16384 | 8192 | 2 | 0 | 0 | 1 | a | b | c | X | X | X | X | X | X | X | X | X | X |
| 8192 | 4096 | 3 | 0 | 0 | 0 | 1 | a | b | c | X | X | X | X | X | X | X | X | X |
| 4096 | 2048 | 4 | 0 | 0 | 0 | 0 | 1 | a | b | c | X | X | X | X | X | X | X | X |
| 2048 | 1024 | 5 | 0 | 0 | 0 | 0 | 0 | 1 | a | b | c | X | X | X | X | X | X | X |
| 1024 | 512 | 6 | 0 | 0 | 0 | 0 | 0 | 0 | 1 | a | b | c | X | X | X | X | X | X |
| 512 | 256 | 7 | 0 | 0 | 0 | 0 | 0 | 0 | 0 | 1 | a | b | c | X | X | X | X | X |
| 256 | 1 | 8 | 0 | 0 | 0 | 0 | 0 | 0 | 0 | 0 | a | b | c | X | X | X | X | X |
| -256 | -1 | 9 | 1 | 1 | 1 | 1 | 1 | 1 | 1 | 1 | a | b | c | X | X | X | X | X |
| -512 | -256 | 10 | 1 | 1 | 1 | 1 | 1 | 1 | 1 | 0 | a | b | c | X | X | X | X | X |
| -1024 | -512 | 11 | 1 | 1 | 1 | 1 | 1 | 1 | 0 | a | b | c | X | X | X | X | X | X |
| -2048 | -1024 | 12 | 1 | 1 | 1 | 1 | 1 | 0 | a | b | c | X | X | X | X | X | X | X |
| -4096 | -2048 | 13 | 1 | 1 | 1 | 1 | 0 | a | b | c | X | X | X | X | X | X | X | X |
| -8192 | -4096 | 14 | 1 | 1 | 1 | 0 | a | b | c | X | X | X | X | X | X | X | X | X |
| -16384 | -8192 | 15 | 1 | 1 | 0 | a | b | c | X | X | X | X | X | X | X | X | X | X |
| -32768 | -16384 | 16 | 1 | 0 | a | b | c | X | X | X | X | X | X | X | X | X | X | X |

| | Compressed (7-bit) 6 | 5 | 4 | 3 | 2 | 1 | 0 |
|---|---|---|---|---|---|---|---|
| 1 | 0 | 1 | 1 | 1 | a | b | c |
| 2 | 0 | 1 | 1 | 0 | a | b | c |
| 3 | 0 | 1 | 0 | 1 | a | b | c |
| 4 | 0 | 1 | 0 | 0 | a | b | c |
| 5 | 0 | 0 | 1 | 1 | a | b | c |
| 6 | 0 | 0 | 1 | 0 | a | b | c |
| 7 | 0 | 0 | 0 | 1 | a | b | c |
| 8 | 0 | 0 | 0 | 0 | a | b | c |
| 9 | 1 | 0 | 0 | 0 | a | b | c |
| 10 | 1 | 0 | 0 | 1 | a | b | c |
| 11 | 1 | 0 | 1 | 0 | a | b | c |
| 12 | 1 | 0 | 1 | 1 | a | b | c |
| 13 | 1 | 1 | 0 | 0 | a | b | c |
| 14 | 1 | 1 | 0 | 1 | a | b | c |
| 15 | 1 | 1 | 1 | 0 | a | b | c |
| 16 | 1 | 1 | 1 | 1 | a | b | c |

| | Expanded (16-bit) 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|
| 1 | 0 | 1 | a | b | c | 0 | 0 | 0 | 0 | 0 | 0 | 0 | 0 | 0 | 0 | 0 |
| 2 | 0 | 0 | 1 | a | b | c | 0 | 0 | 0 | 0 | 0 | 0 | 0 | 0 | 0 | 0 |
| 3 | 0 | 0 | 0 | 1 | a | b | c | 0 | 0 | 0 | 0 | 0 | 0 | 0 | 0 | 0 |
| 4 | 0 | 0 | 0 | 0 | 1 | a | b | c | 0 | 0 | 0 | 0 | 0 | 0 | 0 | 0 |
| 5 | 0 | 0 | 0 | 0 | 0 | 1 | a | b | c | 0 | 0 | 0 | 0 | 0 | 0 | 0 |
| 6 | 0 | 0 | 0 | 0 | 0 | 0 | 1 | a | b | c | 0 | 0 | 0 | 0 | 0 | 0 |
| 7 | 0 | 0 | 0 | 0 | 0 | 0 | 0 | 1 | a | b | c | 0 | 0 | 0 | 0 | 0 |
| 8 | 0 | 0 | 0 | 0 | 0 | 0 | 0 | 0 | a | b | c | 0 | 0 | 0 | 0 | 0 |
| 9 | 1 | 1 | 1 | 1 | 1 | 1 | 1 | 1 | a | b | c | 0 | 0 | 0 | 0 | 0 |
| 10 | 1 | 1 | 1 | 1 | 1 | 1 | 1 | 0 | a | b | c | 0 | 0 | 0 | 0 | 0 |
| 11 | 1 | 1 | 1 | 1 | 1 | 1 | 0 | a | b | c | 0 | 0 | 0 | 0 | 0 | 0 |
| 12 | 1 | 1 | 1 | 1 | 1 | 0 | a | b | c | 0 | 0 | 0 | 0 | 0 | 0 | 0 |
| 13 | 1 | 1 | 1 | 1 | 0 | a | b | c | 0 | 0 | 0 | 0 | 0 | 0 | 0 | 0 |
| 14 | 1 | 1 | 1 | 0 | a | b | c | 0 | 0 | 0 | 0 | 0 | 0 | 0 | 0 | 0 |
| 15 | 1 | 1 | 0 | a | b | c | 0 | 0 | 0 | 0 | 0 | 0 | 0 | 0 | 0 | 0 |
| 16 | 1 | 0 | a | b | c | 0 | 0 | 0 | 0 | 0 | 0 | 0 | 0 | 0 | 0 | 0 |

FIG. 9

IMPLANTABLE INTRA- AND TRANS-BODY WIRELESS NETWORKS FOR THERAPIES

CROSS-REFERENCE TO RELATED APPLICATIONS

This application claims priority as a division under 35 U.S.C. § 121 of U.S. patent application Ser. No. 16/189,862, titled IMPLANTABLE INTRA-AND TRANS-BODY WIRELESS NETWORKS FOR THERAPIES, filed Nov. 13, 2018, that claims priority under 35 U.S.C. § 119 (e) to U.S. Provisional Patent Application Ser. No. 62/585,346, titled IMPLANTABLE INTRA-AND TRANS-BODY WIRELESS NETWORKS FOR THERAPIES, filed Nov. 13, 2017, the contents of which are incorporated herein in their entireties for all purposes.

GOVERNMENT LICENSE RIGHTS

This invention was made with government support under contract number is N66001-15-C-4019 awarded by the Defense Advanced Research Projects Agency (DARPA). The government has certain rights in the invention.

SUMMARY

In accordance with one aspect, there is provided a system of two or more implantable medical devices configured to establish a wireless communication link between the medical devices while implanted in a body of a patient.

In some embodiments, the medical devices are configured to coordinate therapy for the patient through the wireless communication link.

In some embodiments, the medical devices are configured to share data processing load through the wireless communication link.

In some embodiments, at least one of the medical devices is configured to be one of placed in a sleep mode and brought from the sleep mode into an active mode based upon a signal from another at least one of the medical devices.

In some embodiments, the system is configured to establish at least one communication link between at least one of the two or more implantable medical devices and an external device disposed outside of the body of the patient.

In some embodiments, the system is scalable and includes at least an additional implantable medical device having at least one communication link with the external device. The at least one communication link may include a wireless power supply link, a high-speed data link, and a low-speed data link. The two or more implantable medical devices may communicate with the external device utilizing a time-division multiplexing protocol. Each of the two or more implantable medical devices may have different addresses that provide for the external device to communicate separately with each of the two or more implantable medical devices.

In some embodiments, the system is a closed-loop system in which the two or more implantable medical devices are configured to communicate to determine therapy to be applied to the patient in the absence of communication with an external device.

In some embodiments, each of the two or more implantable medical devices have a volume of less than about 2 $cm^3$.

In some embodiments, each of the two or more implantable medical devices includes up to 32 different communication channels configured to one of receive sensor data signals or transmit stimulation signals. The communication channels may be reconfigurable while the implantable medical devices are implanted in the patient by transmission of a down link control signal to the implantable medical devices.

In some embodiments, the two or more implantable medical devices include communications security algorithms including user authentication requirements.

In some embodiments, the two or more implantable medical devices are operable to read signals from nerve tissue of the patient and process the signals to provide outputs to control a prosthetic device of the patient.

In some embodiments, the two or more implantable medical devices are configured to operate with mixed monopolar and bipolar stimulation modes.

In accordance with another aspect, there is provided a system of two or more implantable medical devices configured to establish a wireless link between the two or more implantable medical devices and a device external to a body of a patient while the two or more implantable medical devices are implanted in the body of the patient.

In some embodiments, the two or more implantable medical devices are further configured to establish a communication link between each other while implanted in the body of the patient utilizing an intra-body wireless communication link. The two or more implantable medical devices may be configured to coordinate therapy for the patient through the communication link between each other. The two or more implantable medical devices may be further configured to share data processing load through the communication link between each other.

In some embodiments, the device external to the body of the patient is configured to coordinate therapy for the patient performed by the two or more implantable medical devices.

In some embodiments, the device external to the body of the patient is configured to coordinate monitoring of one or more physiological parameters of the patient by the two or more implantable medical devices. Coordinating monitoring of the one or more physiological parameters of the patient may include aggregating data acquired by the two or more implantable medical devices to produce aggregated data regarding the one or more physiological parameters of the patient. The device external to the body of the patient may be further configured to coordinate therapy for the patient performed by the two or more implantable medical devices based on the aggregated data. The device external to the body of the patient may be further configured to provide the aggregated data to a diagnostic system distinct from the system. The device external to the body of the patient may be further configured to provide a recommendation for treatment of the patient based on the aggregated data.

In some embodiments, the two or more implantable medical devices are configured to share data processing load through the wireless communication link with the device external to the body of the patient.

In some embodiments, at least one of the two or more implantable medical devices is configured to be one of placed in one of a plurality of low power modes and brought from the one of the plurality of low power modes into an active mode based upon a signal from another of the two or more implantable medical devices.

In some embodiments, the system is scalable and includes at least an additional implantable medical device having at least one communication link with the device external to the body of the patient. The system may automatically adapt to activation, deactivation, addition, or removal of an implantable medical device from the system to coordinate monitoring and therapy of the patient utilizing each active implantable medical device implanted in the patient.

In some embodiments, the at least one wireless link includes a wireless power supply link, a high-speed data link, and a low-speed data link. The high-speed data link may be an asymmetrical data link that uplinks data received from sensors in the body of the patient by the two or more implantable medical devices to the device external to the body of the patient. The low-speed data link may be an asymmetrical data link that downlinks configuration settings from the device external to the body of the patient to the two or more implantable medical devices.

In some embodiments, the low-speed data link comprises signals generated by modulating current passing through the power supply link. The low-speed data link and the high-speed data link may be provided in a single signal. The device external to the body of the patient may include a plurality of antennas and may be configured to determine which of the two or more implantable medical devices transmitted a signal over one of the high-speed data link or the low-speed data link based on a known location of the two or more implantable medical devices and a timing of receipt of the signal at different antennas in the plurality of antennas.

In some embodiments, the two or more implantable medical devices communicate with the device external to the body of the patient utilizing a time-division multiplexing protocol.

In some embodiments, each of the two or more implantable medical devices have different addresses that provide for the device external to the body of the patient to communicate separately with each of the two or more implantable medical devices.

In some embodiments, the system is a closed-loop system in which the two or more implantable medical devices are configured to communicate to determine therapy to be applied to the patient in the absence of communication with an external device.

In some embodiments, each of the two or more implantable medical devices have a volume of less than about 4 $cm^3$.

In some embodiments, each of the two or more implantable medical devices includes up to 32 different channels to tissue interfaces configured to one of receive sensor data signals or transmit stimulation signals. The operating parameters of the channels may be reconfigurable, while the two or more implantable medical devices are implanted in the patient, for each of sensing and stimulation by transmission of a down link control signal to the two or more implantable medical devices.

In some embodiments, the two or more implantable medical devices include communications security algorithms including authentication requirements. The two or more implantable medical devices may include communications security algorithms further including encryption.

In some embodiments, the two or more implantable medical devices are operable to read signals from nerve tissue of the patient and process the signals to provide outputs to control an electronic device. The electronic device may include a prosthetic device of the patient. The electronic device may include a computer system distinct from the system. The device external to the body of the patient may be further configured to receive an input from the computer system and adjust one or more operating parameters of one of the device external to the body of the patient or the two or more implantable medical devices responsive to receiving the input from the computer system.

In some embodiments, the two or more implantable medical devices are reconfigurable, while the two or more implantable medical devices are implanted in the patient, to operate with mixed monopolar and bipolar stimulation modes by transmission of a down link control signal to the two or more implantable medical devices.

In some embodiments, the two or more implantable medical devices are reconfigurable, while the two or more implantable medical devices are implanted in the patient, to switch between performing differential signal recording and performing single-ended signal recording by transmission of a down link control signal to the two or more implantable medical devices.

In some embodiments, the two or more implantable medical devices are further configured to establish a communication link between each other while implanted in the body of the patient utilizing a wired communication link.

DESCRIPTION OF THE DRAWINGS

The accompanying drawings are not intended to be drawn to scale. For purposes of clarity, not every component may be labeled in the drawings.

In the drawings:

FIG. 9 illustrates the effect of compression algorithms on data measurements acquired by an embodiment of a wireless implant;

DETAILED DESCRIPTION

Figure 1:
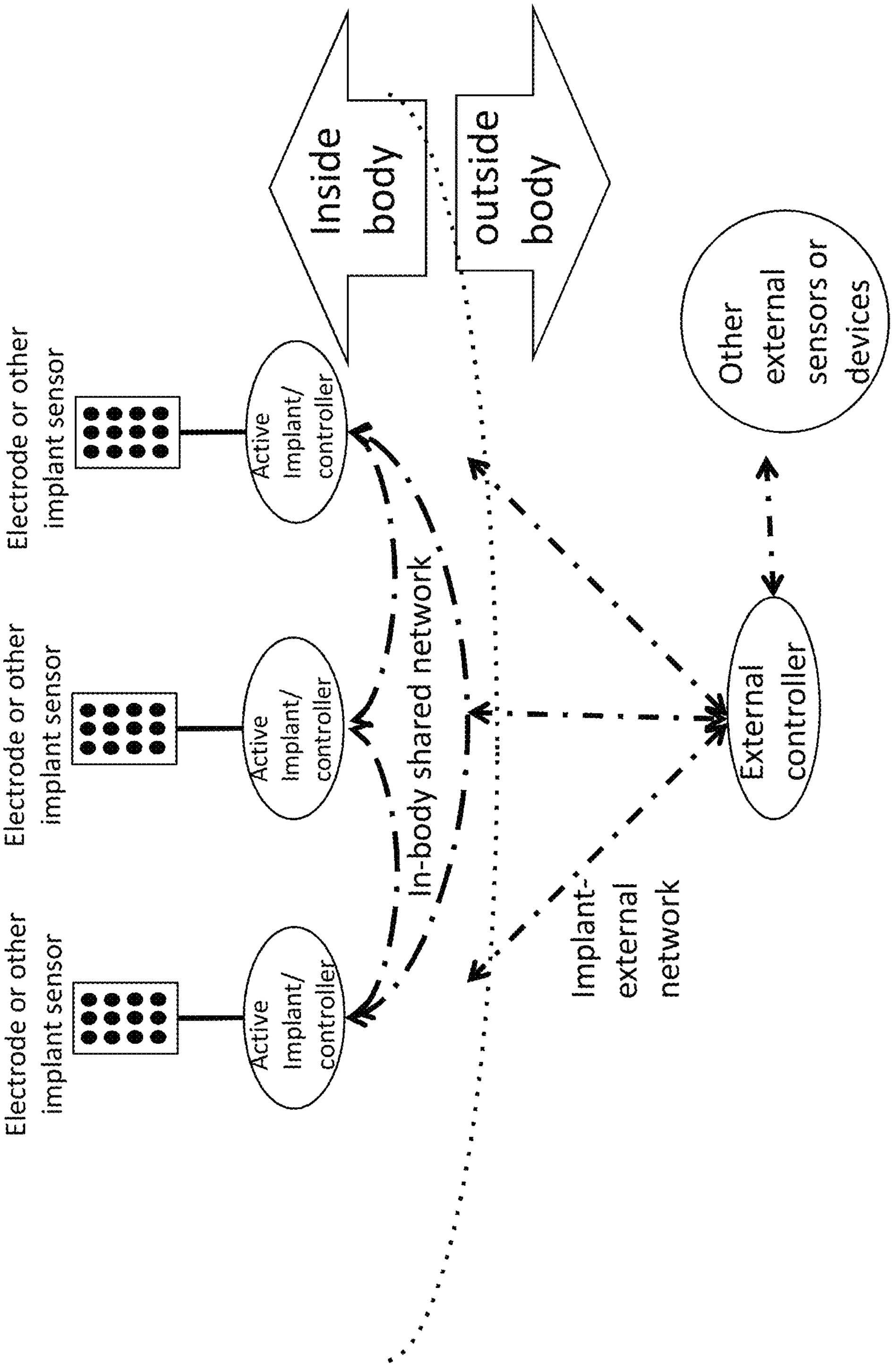
FIG. 1 illustrates a system including implanted therapy/diagnostic devices linked by a communications network with the body of a patient.

Emerging applications in neuromodulation are increasingly involving responsive closed-loop stimulation that is coordinated across distributed targets in the body. A driving factor in the design of new medical implants is the growing awareness that disease often involves complex interactions between multiple systems in the body. This networked perspective has led to the emergence of the fields of networked physiology and networked medicine. However, most chronic implants today resemble pacemakers of the past—large, open-loop, and limited to stimulation or recording at single locations. Key technical challenges overcome by aspects and embodiments disclosed herein include high-fidelity stimulation and recording, miniaturized hermetic packaging, wireless connectivity for power and data, and wireless security.

Current state-of-art complex implantable devices for therapy operate individually or based on input from an external (non-implanted) device. No system or method exists to allow implanted therapy devices to coordinate activity or share information.

Aspects and embodiments disclosed herein include systems of one or more wirelessly connected implants capable of providing electrical stimulation and/or recording of electrical signals in muscles or nervous tissue in the body. Aspects end embodiments of the wireless implants disclosed herein may be far smaller than previously known implants, for example, having a volume of about 4 $cm^3$, 2 $cm^3$, 1 $cm^3$, or less.

Systems and methods for modulating a physiological process are provided. The systems and methods may provide a more effective technique for neurostimulation or neuromodulation therapies than previously known systems. The systems and methods may be used for neurostimulation or neuromodulation in spinal cord, vagus nerve, deep-brain, and retinal applications. The systems and methods may also be used for sensing and modulating activity of other biological organs and systems, including, but not limited to, cardiac muscle, skeletal muscle, bone, and blood vessels. Signals of interest include electrical, magnetic, optical, chemical, and mechanical. The systems and methods may provide improved therapy or treatment than previously known systems by coordinating treatment or therapy across multiple implanted devices.

In some embodiments, each implant is wirelessly powered and equipped with advanced microelectronics (ASICs) that provide 32 channels of recording and stimulation. In other embodiments, each implant may be provided with greater than 32 channels of recording and stimulation. Recorded biosignals can be monitored by distributed implants, processed individually or as aggregates, and used to trigger coordinated stimulation therapies on-the-fly to target disease in ways not previously possible. Each implant can interface with multiple types of tissue interfaces, including electrodes and optical waveguides, and the number of networked implants can be varied based upon the patient's clinical needs. Some embodiments of systems disclosed herein support networking among as many as four wireless implants for a total of 128 electrodes. Each wireless implant may be fully reconfigurable for differential and single-ended recording as well as mono- and multi-polar stimulation with arbitrary waveforms. Embodiments of wireless implants disclosed herein may operate with mixed monopolar and bipolar stimulation modes. Custom ASICs, dense printed circuit board (PCB) design, and miniaturized hermetic packaging enable a compact implantable volume of about 2 $cm^3$, 1 $cm^3$, or less.

The small size of the implants disclosed herein provides for them to easily go where other implants can not—for example, the head or smaller anatomy. Existing deep brain stimulation (DBS) systems are large—typically 20 cc—and require implantation in the chest with an electrode lead tunneled through the neck and head to access the brain. However, many brain disorders, like neuropsychiatric illnesses, affect multiple distributed neural regions that can't all be accessed by existing systems. The network capability of the implants disclosed herein may provide new opportunities to restore balance to these brain networks.

Potential peripheral applications that can benefit from distributed systems include hypertension, diabetes, incontinence, pain, reanimation of paralyzed limbs, and restoration of limb function for amputees through neuroprosthetics.

Features of aspects and embodiments of the wireless medical implants disclosed herein exhibit small volumes and form factors that eases surgical implantation into smaller spaces than previously possible. A single wearable antenna module may wirelessly power, communicate, and control multiple wireless implants, for example, up to four different implants or more. Use of a single wearable antenna to power and control multiple implants eases the burden of use for patients compared to multiple external antenna modules. A system including the external antenna module and wireless implants requires robust power and data links that are tolerant to antenna misalignment. Data compression enables low-power real-time streaming of neural data. In some embodiments, each implant may include up to 32 re-configurable channels (128 re-configurable channels for a system including four networked implants). In some embodiments, the wireless implants may support multiple types of electrode types, for example, Micro-, ECoG, DBS, Cuff, and EMG electrode types. Each implant may include functional reconfigurability. Every channel can switch between recording and stimulation on demand while the implants are implanted in a body of a patient. Recording parameters of the implants that may be adjusted include bandwidth, sampling rate, and single-ended or differential recording modes. Stimulation parameters of the implants that may be adjusted include selection from four independent current sources, and ability to generate arbitrary waveforms. Embodiments of the implants disclosed herein may provide for stimulation artifact suppression. Inherent isolation between different implants eliminates electrical ground artifacts that are common when recording during and immediately after stimulation. Each implant may feature an amplifier with a ±20 mV dynamic input range that avoids saturation ringing and fast-settle circuitry that permits high-fidelity recording within 400 μs of stimulation.

The systems and methods of the present disclosure may be utilized alone or in combination with a larger system that may be used for physiological treatment or for diagnostic purposes. The systems and methods of the present disclosure may be utilized to gather information, control an external computer interface, or treat a subject over a predetermined period of time, or may be used indefinitely to monitor or treat a subject. It may be used to monitor a subject, or control a physiological condition of a subject, or induce or block a certain physiological event. One or more components of the systems and methods of the present disclosure may be used in a wireless configuration.

Various aspects and embodiments disclosed herein relate to networked therapy or diagnostic implants, and potentially external devices, for example, external sensors or controllers, which can together allow for better patient therapies.

The proposed architecture includes two or more implanted devices which can coordinate activities together. A wireless data link between the networked implants allows the devices to share information related to data collected or intended actions.

One example of the benefit of a network like this is the ability for the network of intra- and trans-body implants to share processing responsibility. This means that data collected on one implant could be processed on another or that data could be shared and simultaneously processed by both. This system could lead to more complex or more efficient data processing.

In addition, the network could use signaling between the implants to provide therapy across the network. In a closed-loop network for neuroprosthetics or disease-treating implants, this would mean that the network of implants would communicate over a wireless link to coordinate therapy in the relevant areas based on information collected from any one of the networked implants. In neuroprosthetics, these devices could be placed either near one another in a local part of the body and communicate over short distances or they could be placed globally across the entire body and relay information across the whole body.

Another advantage that the proposed intra- and trans-body networked implants offer is the ability to save power by coordinating between them which units are required for the relevant task. Instead of all implants requiring full power at all times, the networked implants could wake each other up and shut each other down in a closed-loop mode based on external stimuli. Additionally or alternatively the different implants in a system may be activated sequentially in a time-division multiplexing methodology in accordance with a timer included in the system. A first implant may transition from a sleep to a wake mode to perform a desired task during a first time period and then transitions to a sleep mode and a next of the implants transitions from a sleep to a wake mode during a second time period (overlapping or non-overlapping with the first time period) to perform a desired task and then returns to a sleep mode and a next of the implants transitions from a sleep to a wake mode during a third time period, and so on.

Another way to solve this problem without the use of wirelessly networked implants is to use wired, or leaded, implantable systems. While this solution does allow the implants to be networked together, it may be less safe and uncomfortable for the patient than wireless implementations and may involve more complex surgery to ensure the leads traverse the body safely. The addition of wired links and associated connectors further increases modes of failure for the implantable system, which are avoided with the wireless network.

In addition, an external device could handle the communication to and from each of the active implants thereby providing a link between the implants. However, in this embodiment, energy may be wasted transmitting information to an external entity only to have it be re-transmitted to another implant. In addition, this embodiment may involve bulky hardware to be worn by the user as opposed to housing the entire system in the patient.

Creating an intra- and trans-body wireless networks for therapies allows the implants to carry out more complex tasks than when not networked, including distributed processing, collective triggering, and coordination of therapies.

In some embodiments, the networked implants act together as an individual larger unit. In further embodiments, the implanted networked implants are part of a system having a dual network topology, allowing communication between the implants and with external devices as well.

As illustrated in FIG. 1, a plurality of networked therapy or diagnostic implants may be implanted with the body of a patient, for example, a human patient. Although three networked therapy or diagnostic implants are illustrated in FIG. 1, it is to be appreciated that aspects and embodiments of therapy or diagnostic systems disclosed herein are not limited to including three networked therapy or diagnostic implants. The three networked therapy or diagnostic implants may have similar or different functionality. The three networked therapy or diagnostic implants may include one or more sensors and/or one or more electrodes to deliver electrical therapy to the patient. Any one or more of the networked therapy or diagnostic implants may include a controller to provide control commands to circuitry in the same or others of the networked therapy or diagnostic implants. Each of the networked therapy or diagnostic implants may be in communication with another through an in—body shared network, which may be a wireless network or, in some embodiments, may include one or more wired communication links. At least one of, and in some embodiments, each of the networked therapy or diagnostic implants may also be in communication with an external controller through an implant-external network, which may be a wireless communication network. One or more other external sensors may also be in communication with the external controller, via a wired or wireless communication link. One or more other external devices, for example a distinct diagnostic device or computer system may also be in communication with the external controller, via a wired or wireless communication link.

Figure 2A:
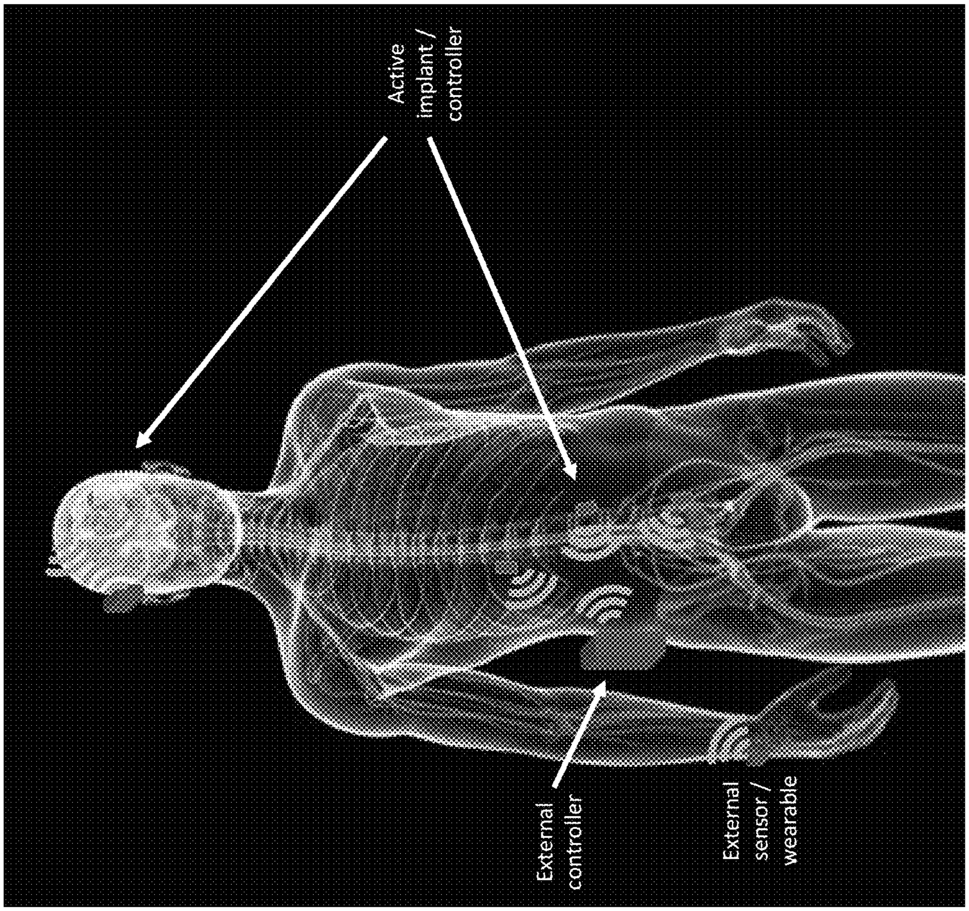
FIG. 2A illustrates an embodiment of a system including therapy/diagnostic/control devices implanted in a human patient and associated external sensors/controllers.
Figure 2B:
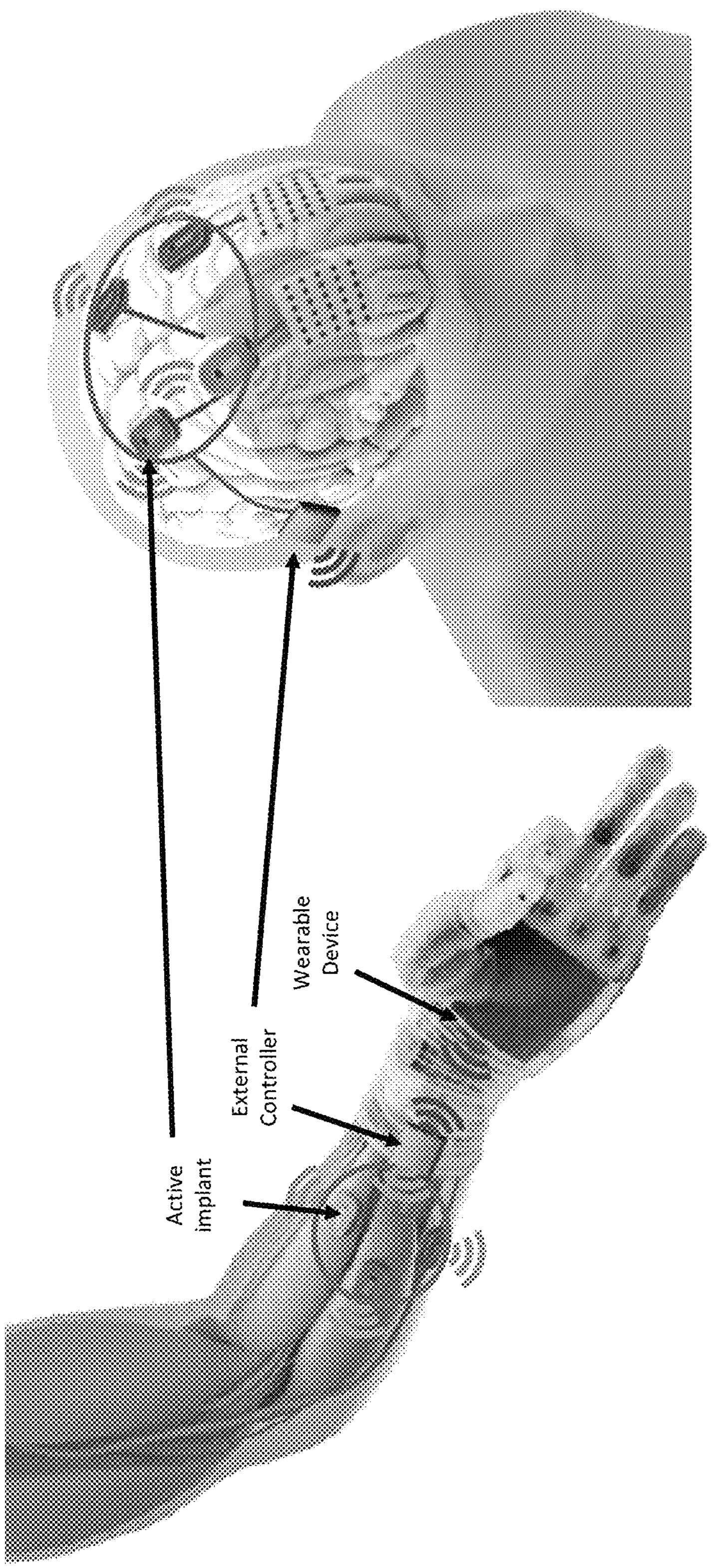
FIG. 2B illustrates another embodiment of a system including therapy/diagnostic/control devices implanted in a human patient and associated external sensors/controllers.

FIGS. 2A and 2B illustrate embodiments of systems including wirelessly networked therapy or diagnostic implants (also referred to herein as implantable medical devices). As illustrated, one or more active networked therapy or diagnostic implants/controllers may be electrically coupled to or otherwise in communication with one or more internal bodily structures of a patient, for example, to nerves in the arm, leg, or brain of the patient. One or more active networked therapy or diagnostic implants/controllers may be in communication with any one or more other of the active networked therapy or diagnostic implants/controllers via, for example, an in—body shared network, which may be a wireless network or, in some embodiments, may include one or more wired communication links. An external controller located outside the body of the patient, for example, in an article of clothing, clipped to a belt, or carried in a holster may be in communication, for example, via a wireless network with one or more of the active networked therapy or diagnostic implants/controllers via, for example, implant-external network, which may be a wireless communication network. One or more other externals sensors, for example a blood pressure, blood oxygen level, temperature, or other type of sensor may also be in communication with the external controller, via a wired or wireless communication link. The external sensors/wearable devices illustrated in FIG. 2A and FIG. 2B are located on the wrist of the patient, but in other embodiments may be located on or proximate other portions of the body of the patient.

Figure 2C:
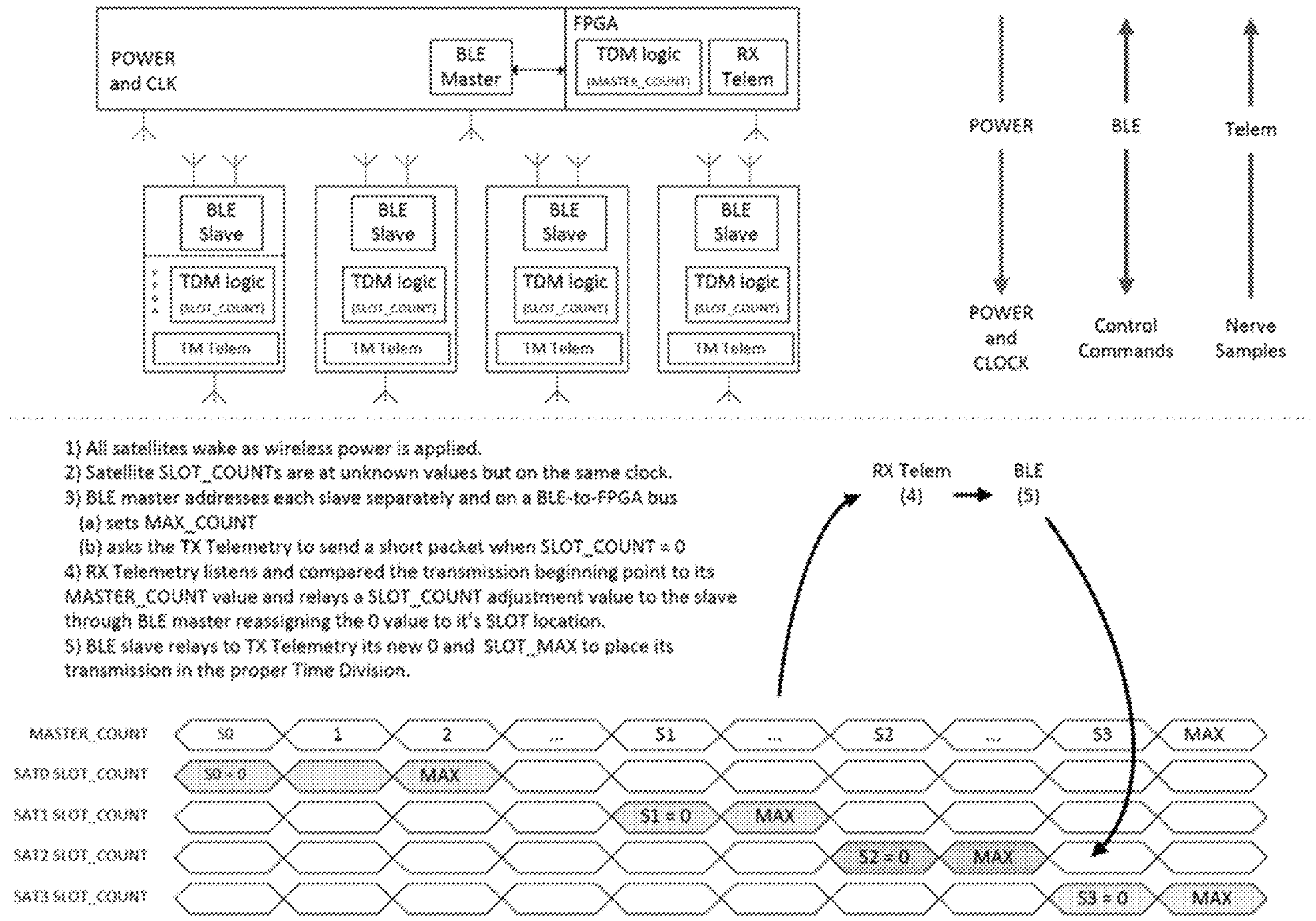
FIG. 2C illustrates a methodology for communications between the implants and the external controller of FIG. 2A or FIG. 2B.
Figure 2D:
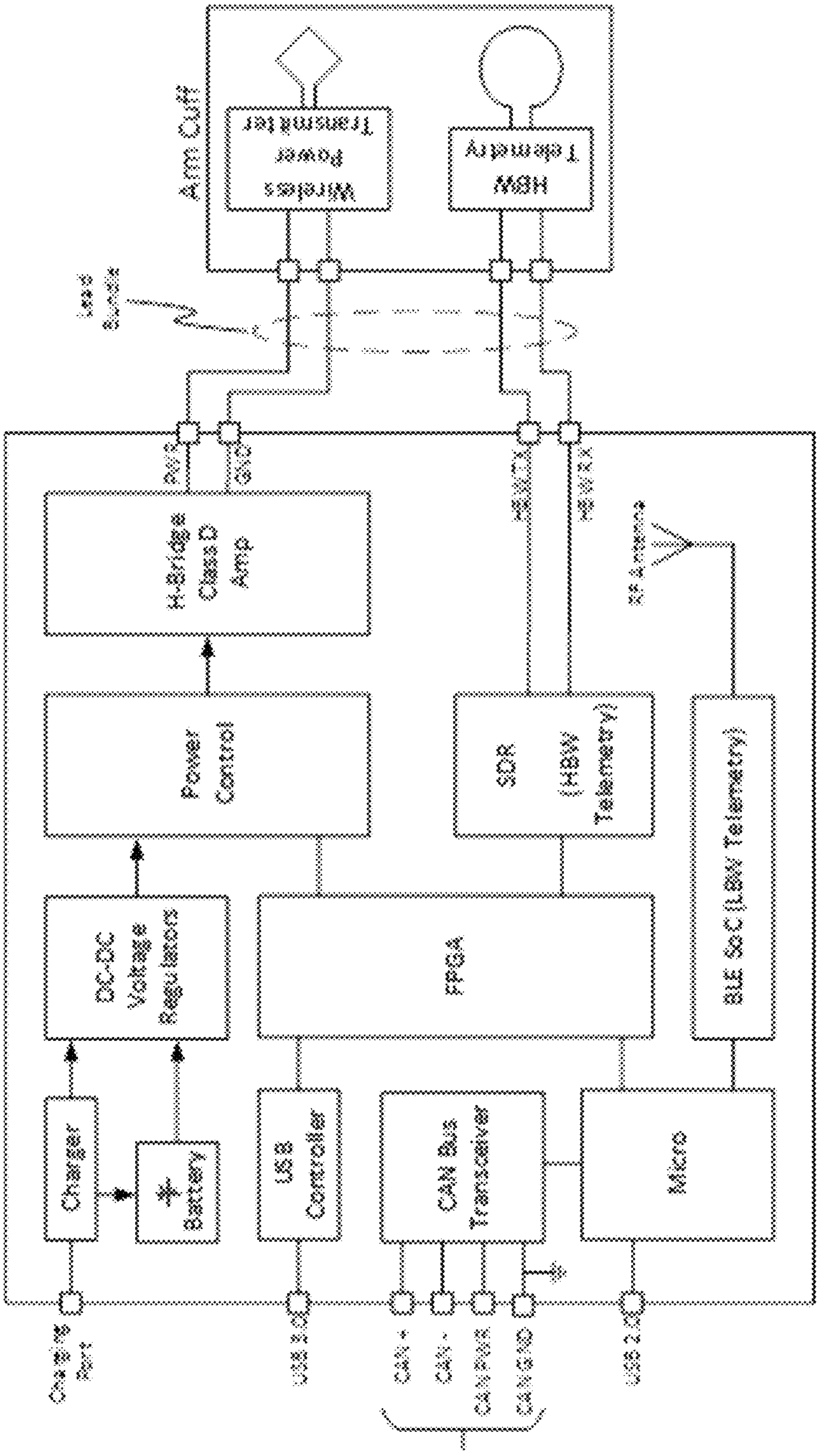
FIG. 2D is a block circuit diagram of an example of an external controller of the system of FIG. 2A or FIG. 2B.

Command and control of the wireless implants may be performed over a wireless low-bandwidth RF radio, which could be implemented with Bluetooth® Low Energy, or a similar technology. To establish a hierarchical wireless network, the external controller is implemented as the master and the implants are implemented as slaves. Messages are sent from the external master to each implanted slave to set up allocated time slots for each implant to transmit data back to the master using a second high-bandwidth RF radio that operates at a separate frequency that does not interfere with the low-bandwidth link. While operating as slaves over the low-bandwidth link, implants listen to communication from the external device and await messages that are addressed to them. Each implant may be separately addressed by the external controller to provide power and/or read or send data to each implant separately or at different times. To avoid interference between simultaneous messages sent from implants to the external device, a time-division multiplexing (TDM) scheme may be used, where each implant is allocated a unique period of time in which it can transmit data to the external controller. The relative ordering and length of each implant's timeslot can be adjusted based the number of implants in the network and its data rate in order to achieve optimal system performance. FIG. 2C illustrates a method of communication between four implanted devices (referred to in this figure as "satellites" or "slaves") and an external controller (referred to in this figure as "master") utilizing TDM.

The low-bandwidth radio can be implemented as a bi-directional link (for example, Bluetooth® Low Energy, or similar technology) that permits messages to be passed from master-to-slave and also slave-to-master. Alternatively, the low-bandwidth radio can be implemented as a uni-directional link using modulation of the power signal transmitted to each implant from the external controller, or as modulation of a backscatter carrier that may be used to implement the high-bandwidth link. Data sent from the external controller to the implants may include configuration messages that can establish allocated time slots for transmission across the high-bandwidth link, configure recording settings (for example, electrodes to be recorded from, differential recording vs single-ended, bandwidth, sampling rate, amplifier channel shut-down modes), configure stimulation settings (for example, electrodes to be stimulated on, monopolar vs bipolar vs multi-polar modes, waveform parameters), trigger pre-loaded stimulation sequences or adjust thresholds and algorithm parameters for closed-loop stimulation triggered by internal computation within each implant, and/or request device status information (for example, impedances, voltage levels, humidity, data logs).

The high-bandwidth data link can be implemented as a uni-directional link to stream large quantities of data (for example, physiological recordings) from the implants to the external controller. The high-bandwidth radio can be implemented as an active radio or as a passive backscatter communication link. In the latter, the load or impedance on the implant's backscatter antenna is modulated such that energy that is reflected back the external controller contains encoded information. Data sent from the implants to the external device may include device status, data logs, and detected faults, and recorded data from neurons, muscle, accelerometers, temperature, pH, and other sensors.

The external controller may contain wired and wireless links to other external systems to send control signals (for example, to prosthetic limbs or computers) or receive input signals (for example, from diagnostic devices, prosthetic limbs, or computers). In some implementations, the external controller may be directly wired to separate computerized systems (for example, over a USB, optical, or CAN Bus cable). In other implementations, the external controller may contain a separate wireless link (for example, RF).

A block diagram of one embodiment of an external controller that may interface with wireless implants as disclosed herein through an arm cuff is illustrated in FIG. 2C.

The implant provides an interface to biological tissue (for example, neurons, muscle, and/or bone) via attached electrodes, optrodes, or other sensing and stimulation interfaces. The implant interfaces may be electrical in nature and the types of electrodes that can be used include micro-electrodes, macro-electrodes, cuff, intrafascicular, EMG, DBS, ECoG, paddle, and cardiac leads. A cross-point switch matrix inside each implant allows every channel to be used for recording and stimulation, which can be re-configured on-the-fly. The cross-point switch matrix also allows a bi-polar amplifier to be reconfigured for differential and single-ended recording modalities. Stimulation can be routed to any electrode from stimulation circuitry that provides stimulation waveforms. Multiple stimulation sources may be combined on any electrode to increase the amount of stimulation (for example, increase current).

The implant also contains circuitry for receiving wireless power from the external system. In some cases, a rechargeable battery may be included in the implant. In other cases, the implant receives continuous wireless power without an internal battery.

The implant also contains logic for processing data and implementing closed-loop algorithms that may trigger stimulation in response to data sensed by the implant itself, or in response to aggregated data received from the larger network of implants.

The external system provides an interface between the implanted network, the user (for example, patient or clinician) and peripheral devices (for example, prosthetics, diagnostics, computers, or cloud computing). Data from implants (which may be pre-processed) is aggregated by the external system and algorithms are implemented to control external systems or to provide responsive stimulation therapies that may be distributed throughout the implants.

Figure 3A:
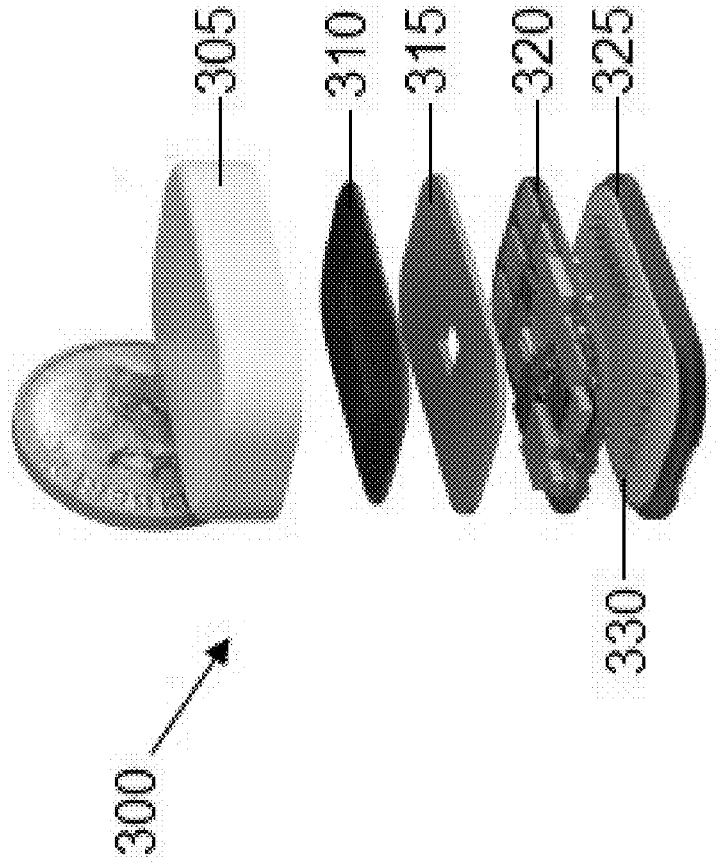
FIG. 3A is an exploded view of an example of a wireless implant.
Figure 3B:
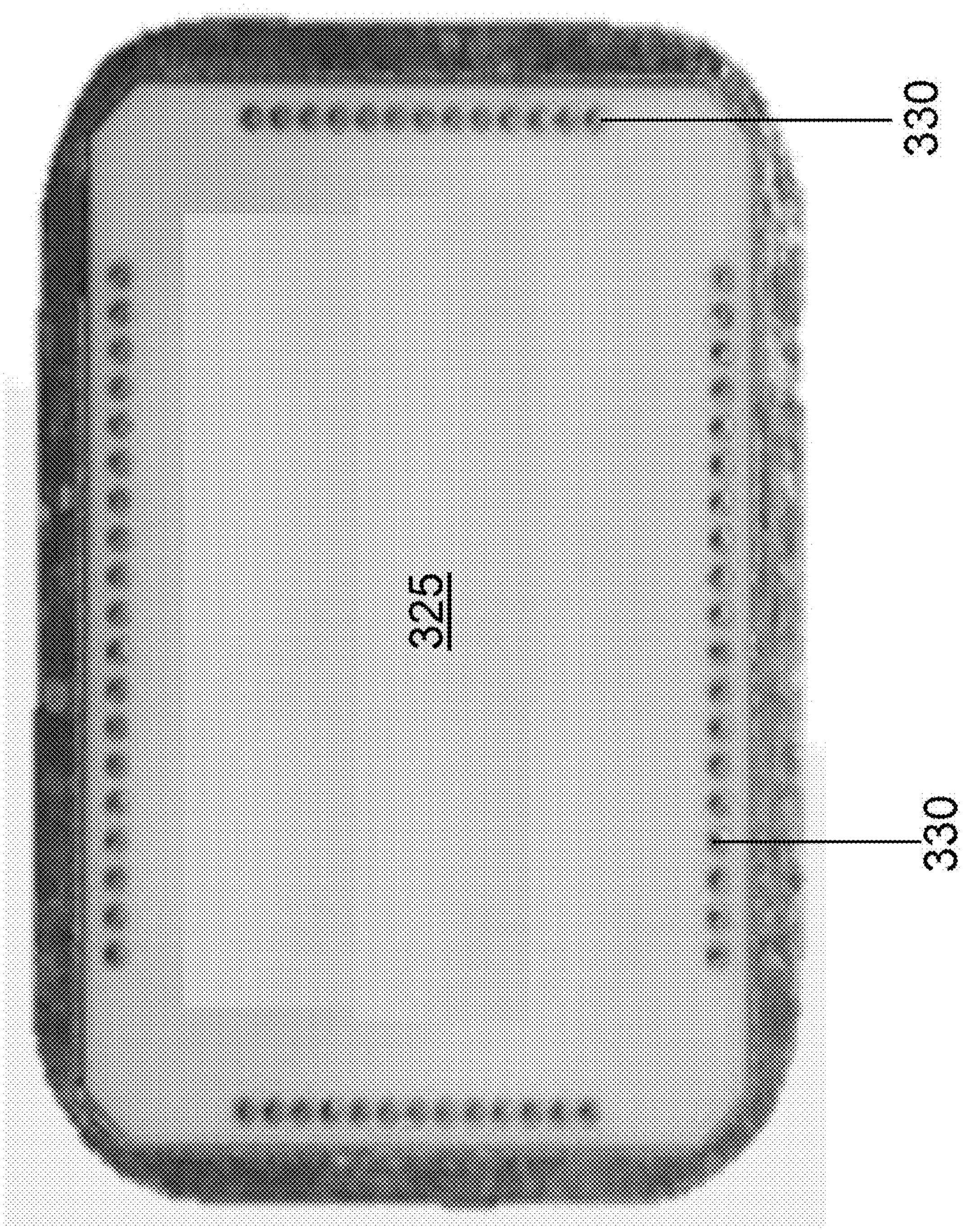
FIG. 3B illustrates external electrical connections on an external surface of the wireless implant of FIG. 3A for electrodes or sensors.

FIG. 3A illustrates an example of a wireless implant 300 that may be utilized in networked implant systems as disclosed herein. The implant 300 is illustrated in an exploded view and a U.S. dime is included to give an indication of size. The implant 300 includes a lid 305, an antenna board including one or more antennas 310, which may include, for example, a inductive power link antenna, a low-bandwidth data link antenna, and a high-bandwidth data link antenna, a ferrite and conductive shield layer 315, a PCB layer 320 including a plurality of ASICs that control operation of the implant, and a feedthrough layer 325. The lid 305 and feedthrough layer 320 may con formed of a biocompatible material such as a ceramic, for example, aluminum oxide or other biocompatible ceramic. The lid 305 and feedthrough layer 325 are hermetically sealed while allowing for wireless communication to and from the circuitry internal to the implant 300. The feedthrough layer 325 may include electrical contacts 330 that provide electrical communication between sensors or electrodes or other stimulation devices external to the implant 300 and the circuitry within the implant 300. The electrical contacts 330 of the feedthrough layer 320 may be formed of a biocompatible conductive material, for example, a metal such as gold, or a platinum-iridium alloy, or any other biocompatible conductive material. Electrical contact 330 on the outside of the feedthrough layer 325 are illustrated in FIG. 3B. In some embodiments, the inductive power link antenna may be a coil disposed within or on the outside of the lid 305 and sealed against the environment internal to the body by, for example, a layer of biocompatible polymer, rather than disposed in the antenna board 310. The wireless implant 300 may be covered in a biocompatible material, for example, silicone, with access apertures for the electrical contacts 330.

Figure 4C:
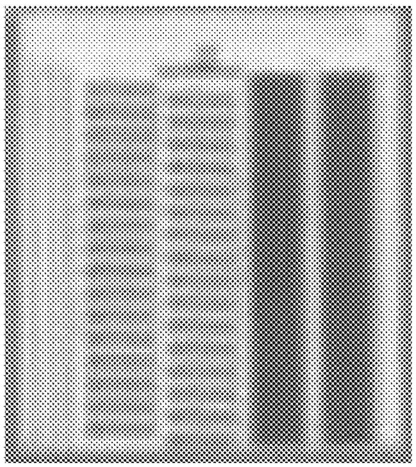
FIG. 4C illustrates a switch matrix chip that maybe included in the wireless implant of FIG. 3A.
Figure 4B:
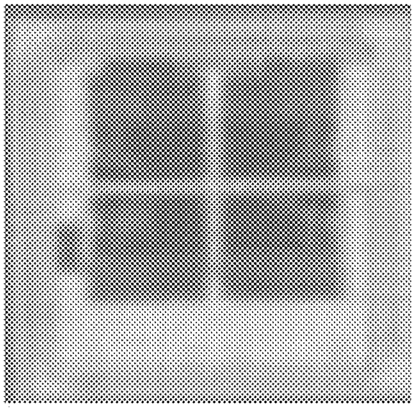
FIG. 4B illustrates a stimulator digital-to-analog converter chip that maybe included in the wireless implant of FIG. 3A.
Figure 4A:
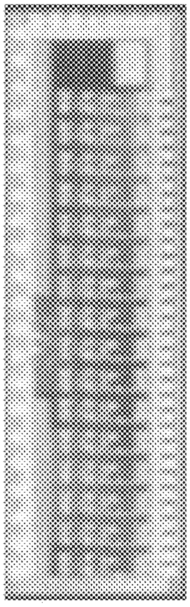
FIG. 4A illustrates an amplifier chip that maybe included in the wireless implant of FIG. 3A.
Figure 4E:
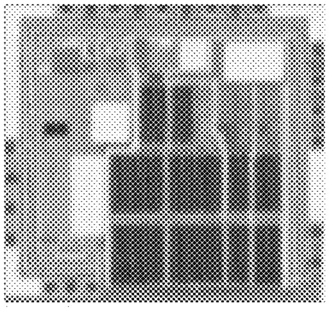
FIG. 4E illustrates a power supply chip that maybe included in the wireless implant of FIG. 3A.
Figure 4D:
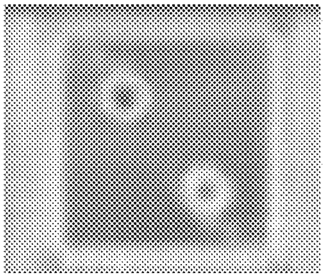
FIG. 4D illustrates a radio chip that maybe included in the wireless implant of FIG. 3A.

Examples of ASICs that may be included in the implant 300, for example, on the PCB layer 320 include one or more amplifiers (FIG. 4A). The one or more amplifiers may each support 32 channels of single ended recording or 16 channels of differential recording. A second ASIC that may be included in the implant 300 is a stimulator digital-to-analog converter (FIG. 4B). The stimulator digital-to-analog converter may include, for example, four channels and be capable of outputting ±10 mA at ±10V. A third ASIC that may be included in the implant 300 is a cross-point switch matrix (FIG. 4C). The switch matrix may support reconfiguration of electrodes for recording or stimulation, with a 70Ω closed circuit impedance an >1 GΩ/open circuit impedance. The switch matrix may support the combination of multiple stimulation channels to increase stimulation output. The switch matrix may support mapping of multiple references to amplifier inputs for combinations of differential and single-ended recordings. A third ASIC that may be included in the implant 300 is a radio circuit (FIG. 4D) that may be utilized for communication between different implants in the body of a subject and/or with an external monitor or controller. The radio circuit may operate at, for example, 915 MHz with a bandwidth of 20 Mbps or more and may operate in accordance with the BPSK/QPSK modulation schemes. A third ASIC that may be included in the implant 300 is a power supply (FIG. 4E). The power supply may receive input power from an inductive power coil in the antenna board 310 and output power at, for example, ±10V, 3.3V, and 1.8V to provide power at appropriate voltages to the other components of the implant. The implant may further include additional integrated circuits, discreet active devices and/or passive devices (for example, capacitors, inductors, and/or resistors) not specifically illustrated.

Figure 4F:
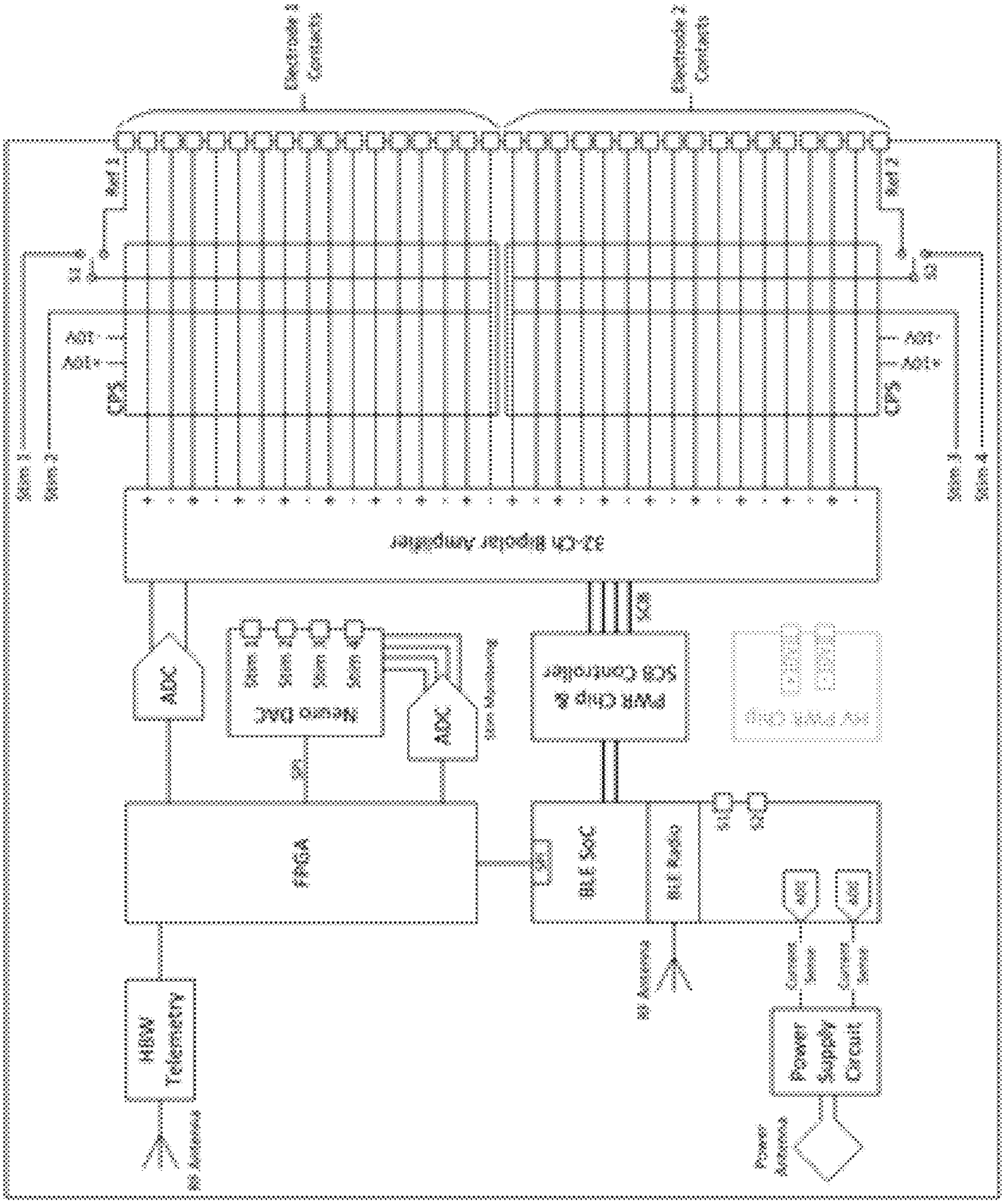
FIG. 4F is a block diagram of circuitry of an example of a wireless implant.
Figure 4G:
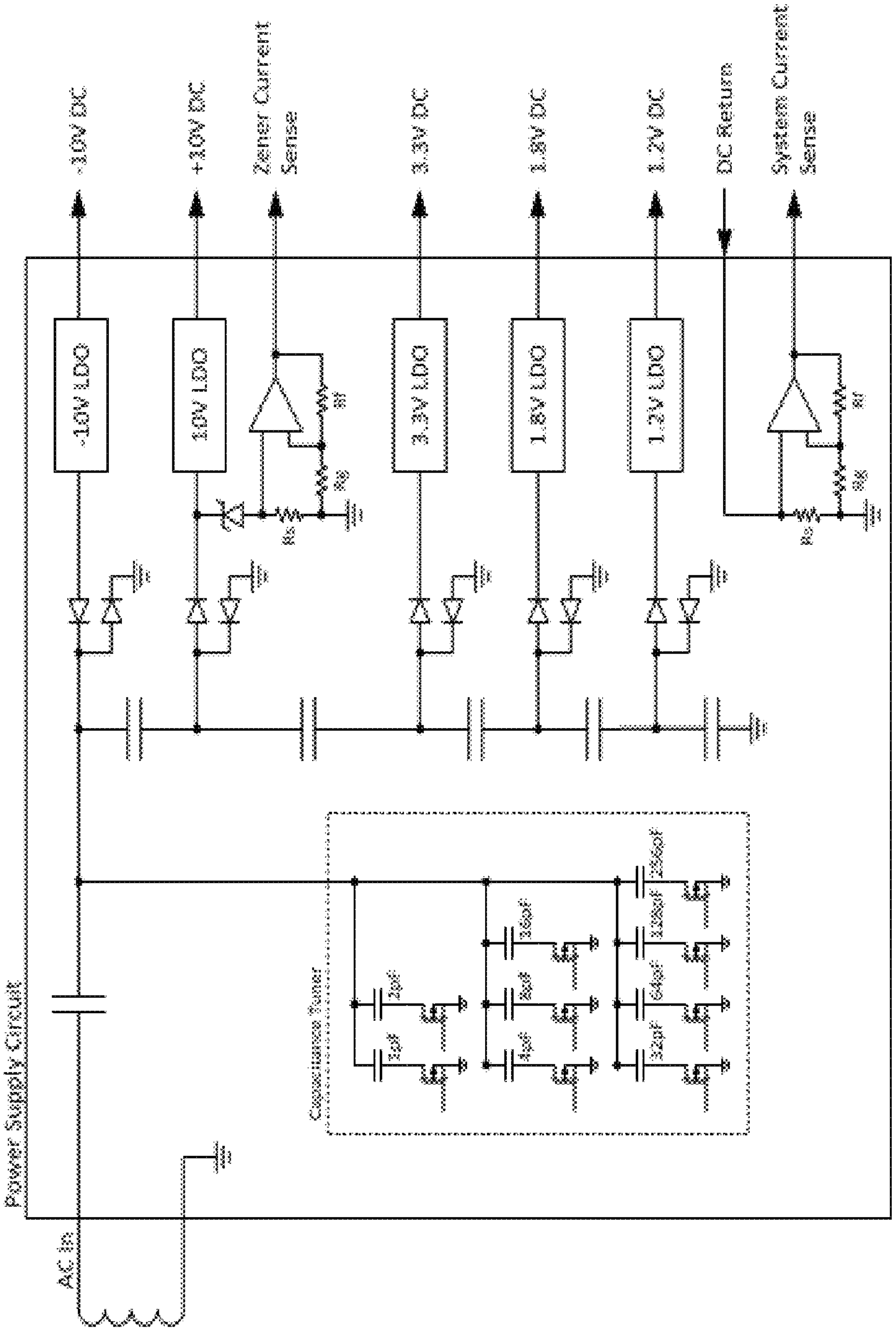
FIG. 4G is a block diagram of a power supply circuit of an example of a wireless implant.

A block diagram of circuitry of an example of a wireless implant is illustrated in FIG. 4F. A block diagram of a power supply circuit of an example of a wireless implant is illustrated in FIG. 4G.

Figure 5:
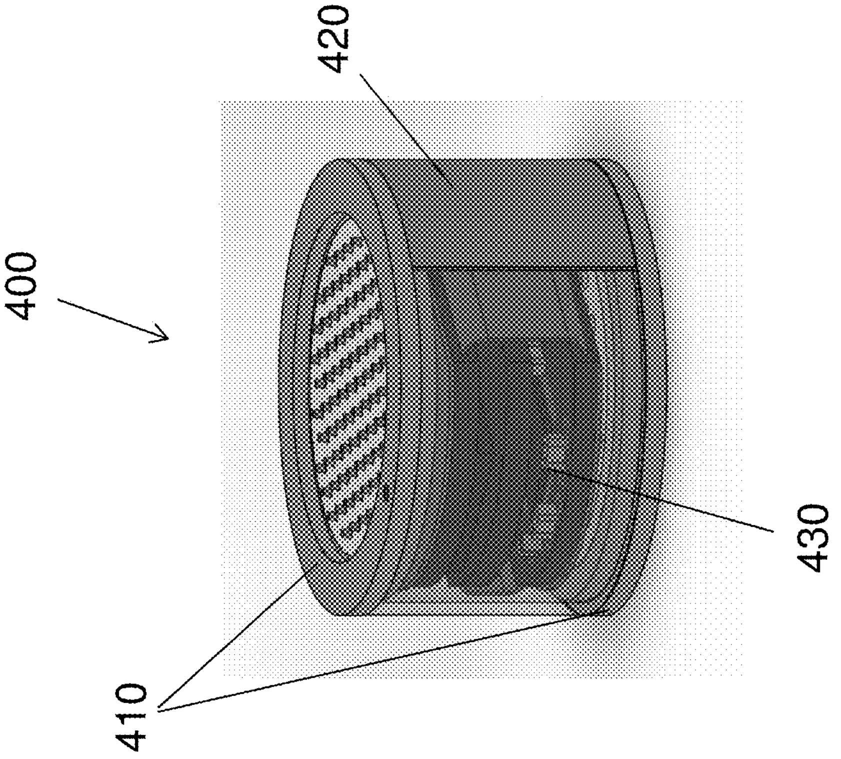
FIG. 5 illustrates another example of a wireless implant.

An alternate form factor for a wireless implant 400 is illustrated in FIG. 5. The wireless implant 400 may comprise a microelectronic printed circuit board 430, a housing 420, and a plurality of feedthroughs 410. The feedthroughs 410 may be oppositely disposed. The wireless implant 400 may be constructed, for example, by fusing the housing 420 with the feedthroughs 410, such that the printed circuit board 430 is encapsulated within the housing 420. The wireless implant 400 is illustrated with a portion of the housing 420 omitted to illustrate the internal circuit board 430. The form factor of the wireless implant 400 is illustrated in FIG. 5 may have a diameter of about 14 mm with a total implantable volume of about 0.7 $cm^3$.

Figure 6:
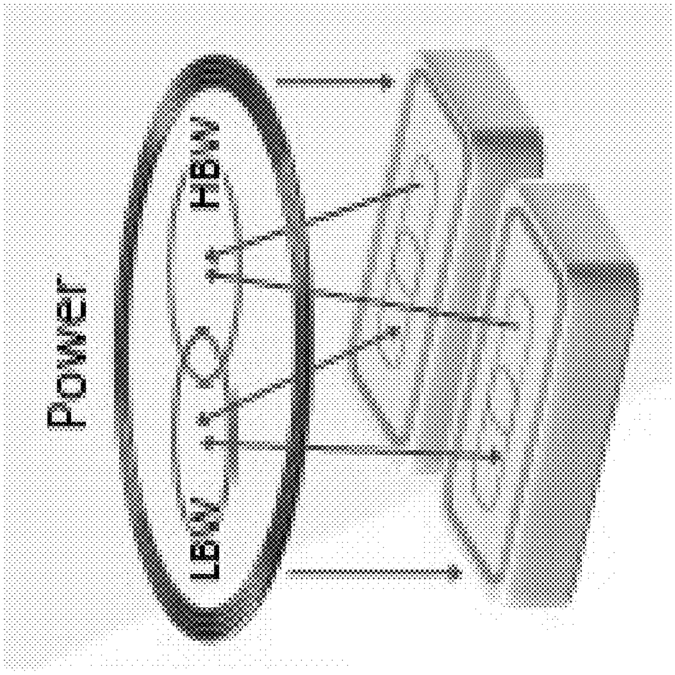
FIG. 6 illustrates wireless links associated with examples of wireless implants.
Figure 7A:
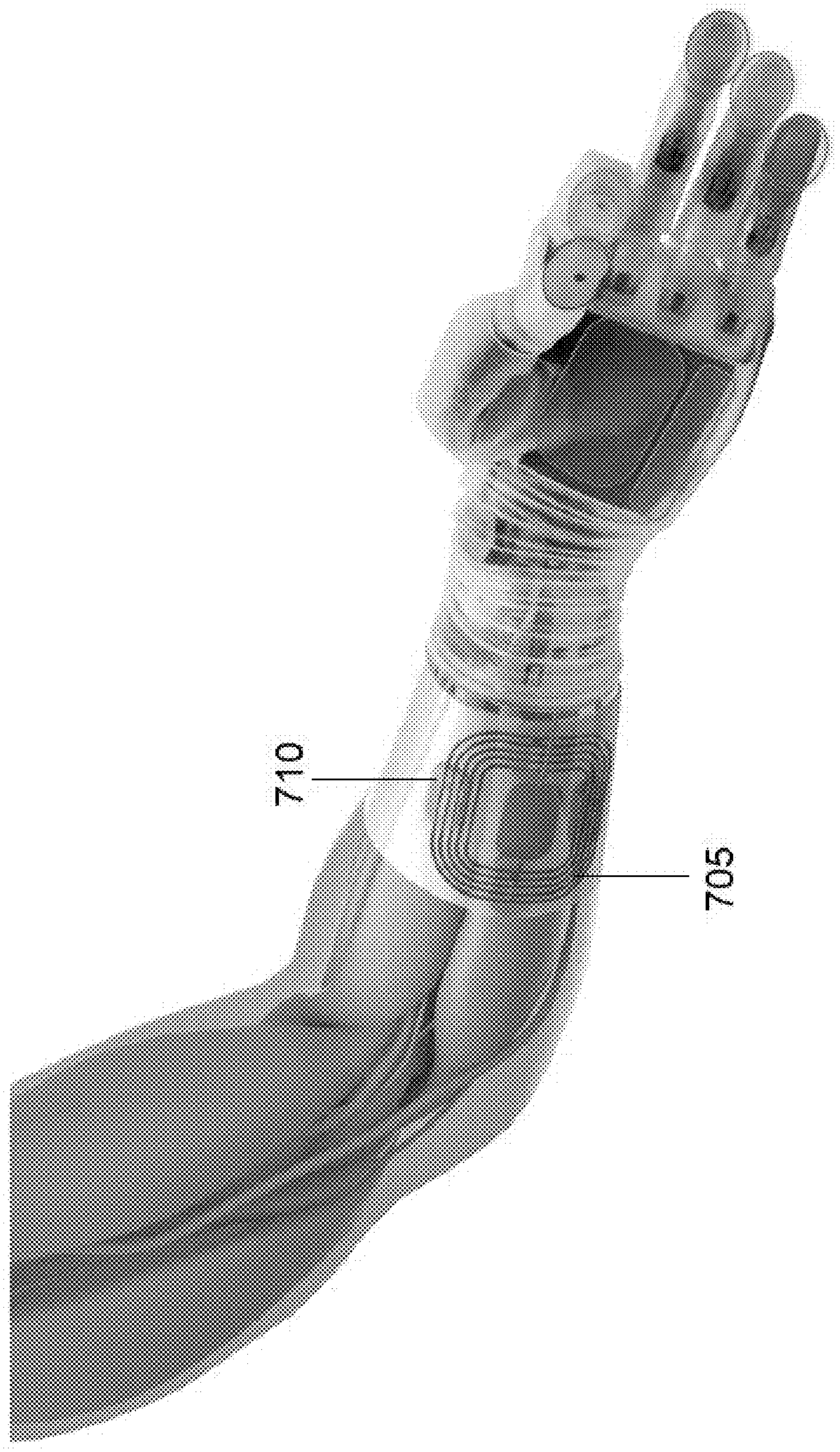
FIG. 7A illustrates an external power coil disposed about an arm of a subject having a prosthetic hand in which four wireless implants are implanted in the arm to read nerve signals and control the prosthetic hand.

Embodiments of the wireless implant disclosed herein may include three robust wireless links that are tolerant to misalignment and rotation. The three wireless links include power, low-bandwidth (LBW) bi-directional data, and high-bandwidth (HBW) uni-directional data streaming. The three wireless links are illustrated schematically in FIG. 6 with a pair of wireless implants. Power to the wireless implants may be provided from an external AC power source (which may transmit power in a radio frequency band that penetrates the body with little attenuation) to an inductive power coil that may be included in the antenna board of the wireless implants or as a separate element of the wireless implants. FIG. 7A illustrates an external power coil 705 disposed about an arm of a subject having a prosthetic hand in which four wireless implants 710 are implanted in the arm to read nerve signals and control the prosthetic hand. The external power coil may be in electrical communication with an external controller, for example, an external controller as illustrated in FIG. 2A or FIG. 2B.

Figure 7B:
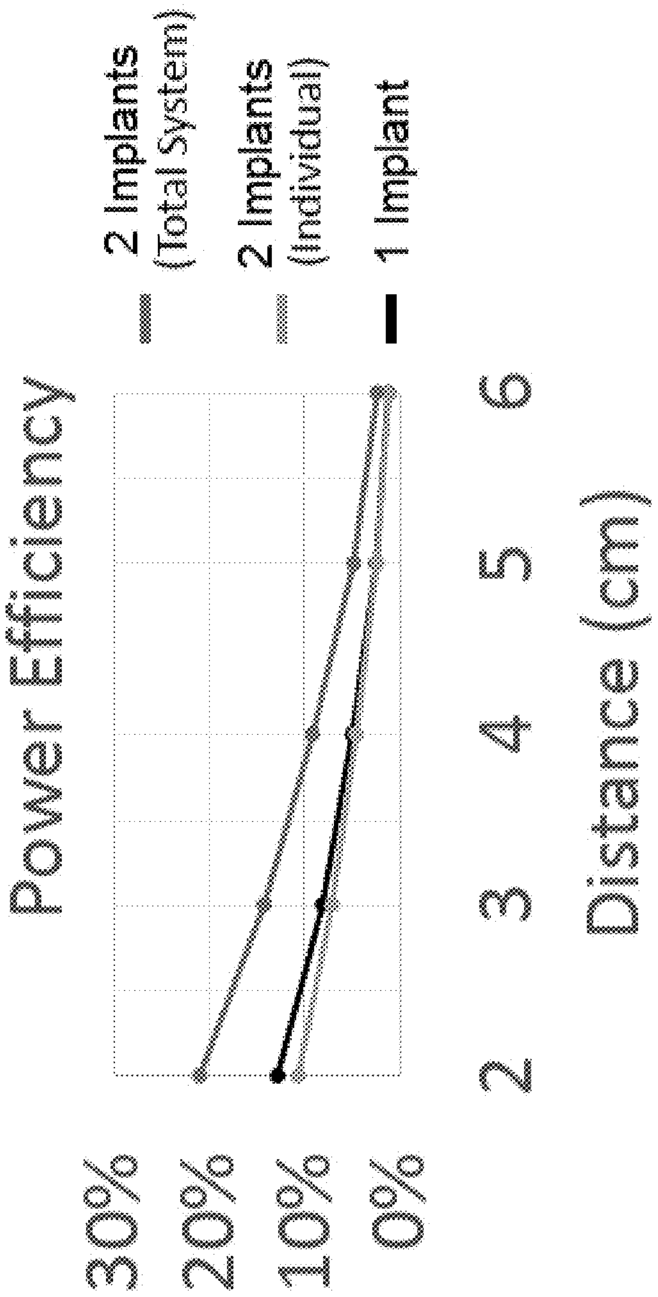
FIG. 7B is a chart of power transfer efficiency between an external power coil and wireless implants.
Figure 7C:
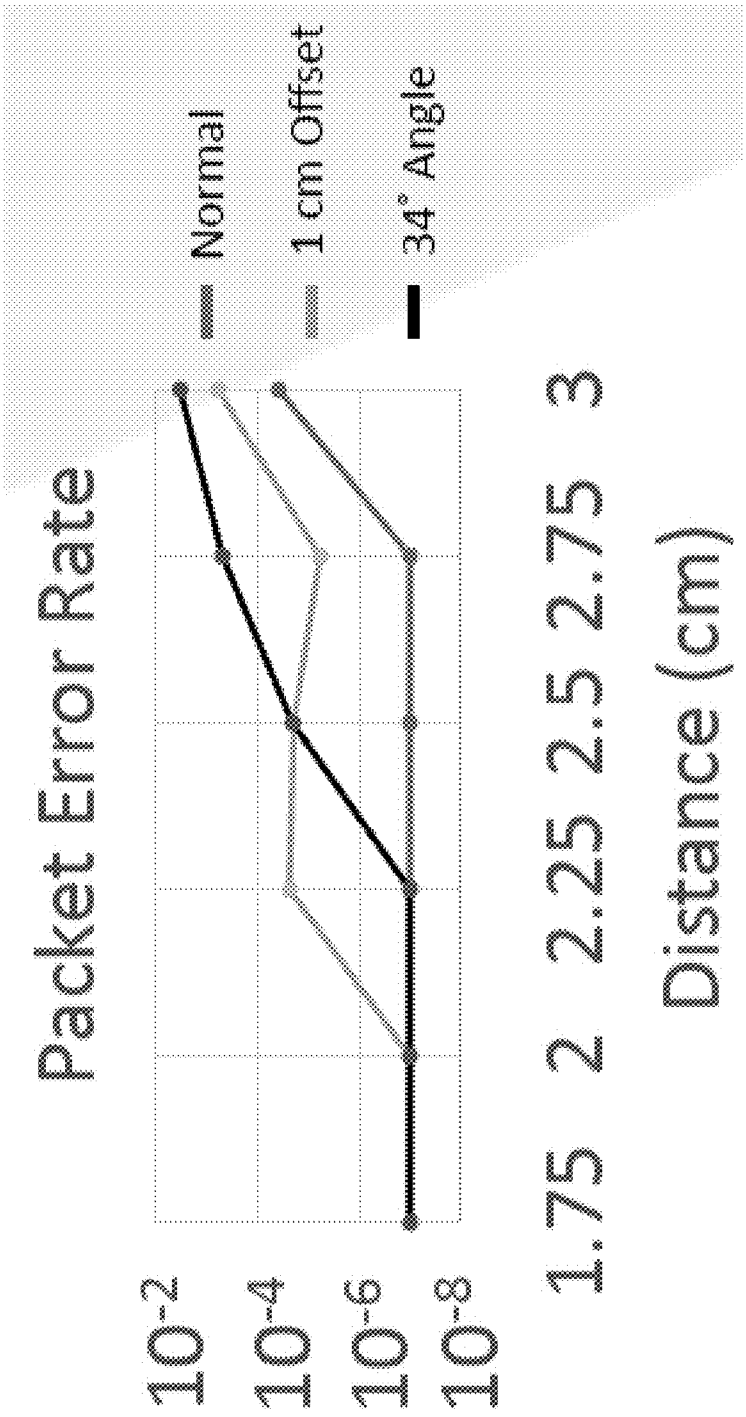
FIG. 7C is a chart of packet error rate in data transmissions to and from a wireless implant.

In some implementations it may be desirable to align the external power coil 705 directly over and in parallel to the power link antenna and/or data link antennas of a wireless implant. In other implementations it may be desirable to wind the external power coil around the body (for example, circumscribing the arm). As illustrated in FIG. 7B, power transfer efficiency between an external power coil and wireless implants may decrease with distance between the external power coil and wireless implants. While the wireless power efficiency between any single implant and the external power coil may decrease as more implants are added to the system, the overall wireless efficiency of the system may increase. As illustrated in FIG. 7C packet error rate in data transmissions to and from a wireless implant in the high bandwidth link may increase with increasing distance between an antenna of an external controller and a wireless implant and/or with a degree of offset or misalignment between the data link antennas of the wireless implant and that of the external controller. Robust data transmission may be improved by implementing error detection and correction (for example, cyclic redundancy checks and automatic repeat requests).

Figure 8A:
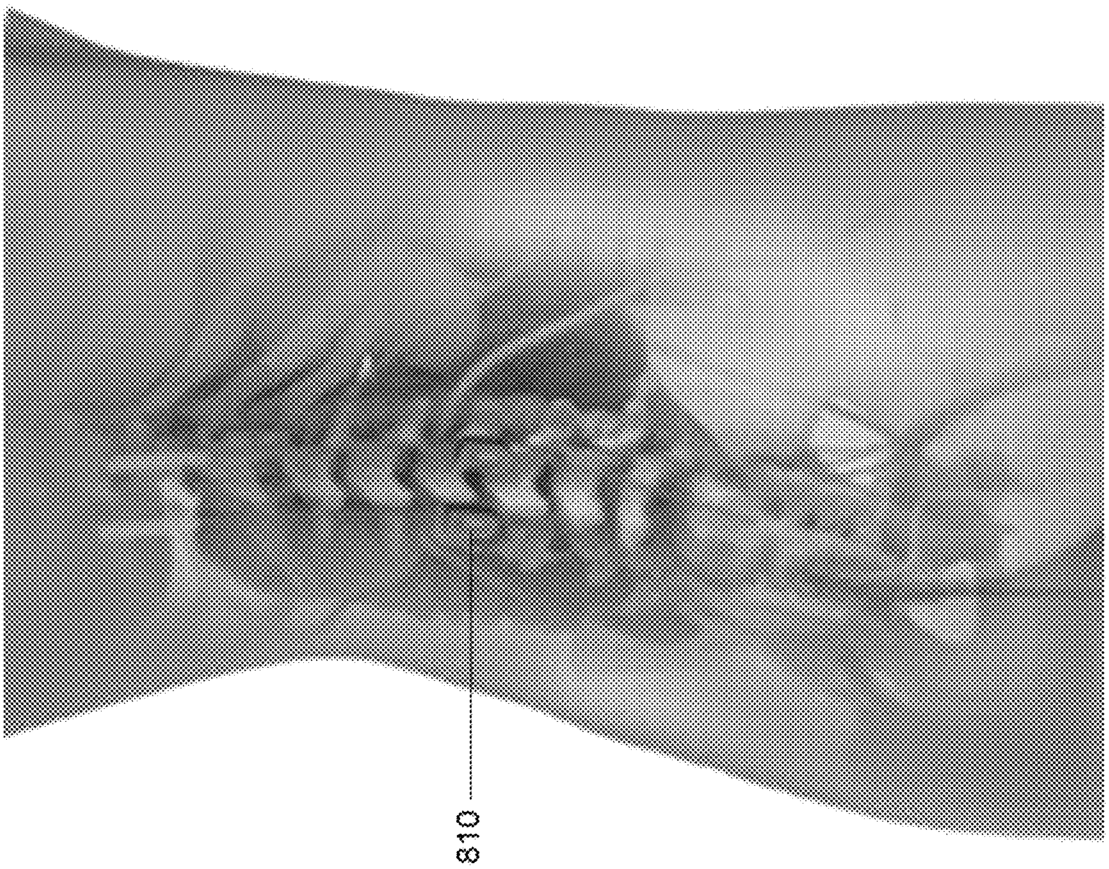
FIG. 8A illustrates wireless implants disposed in the back of a subject.
Figure 8B:
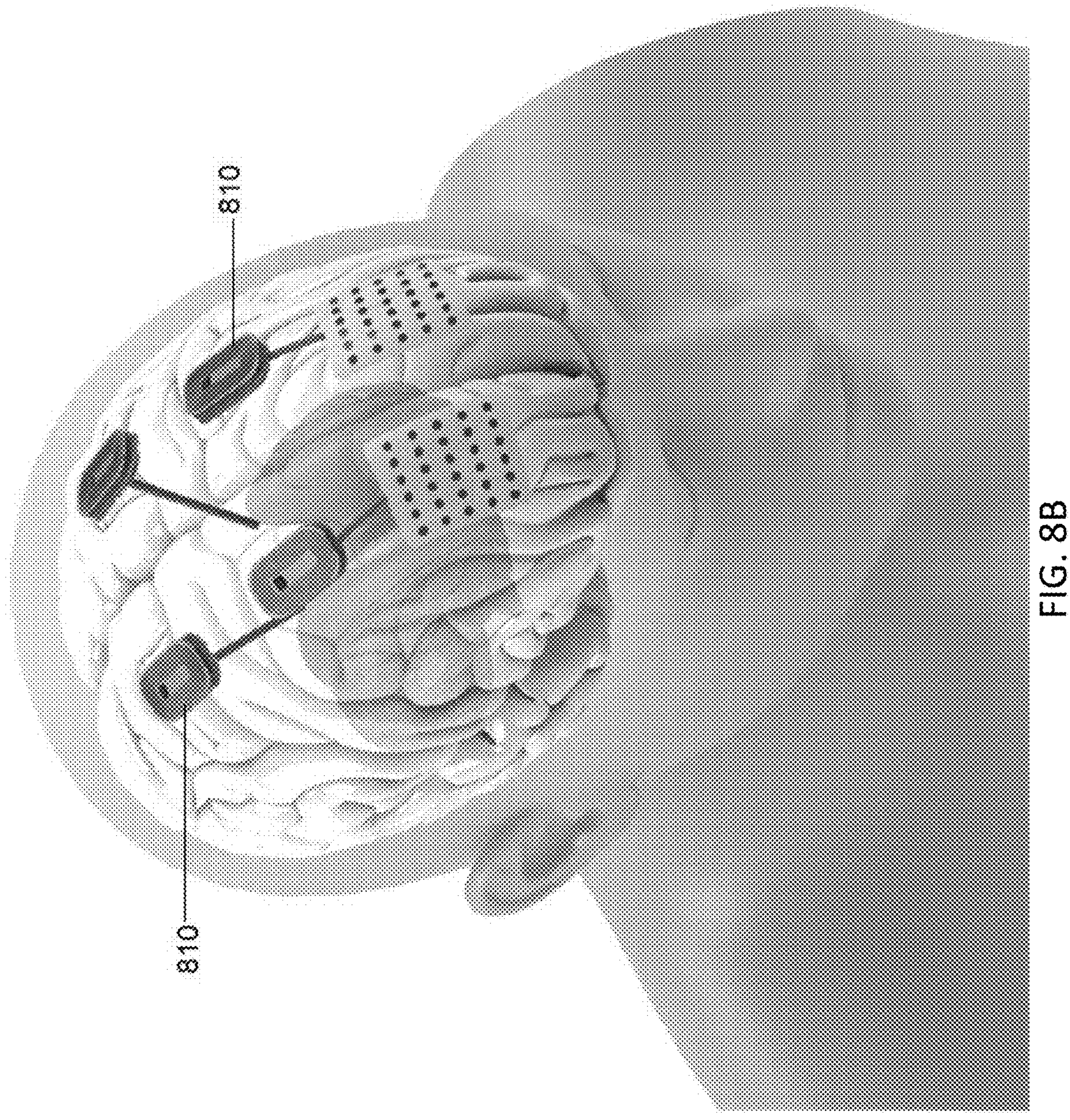
FIG. 8B illustrates wireless implants disposed in the head of a subject.

FIGS. 8A and 8B illustrate alternate examples of placement of wireless implants disclosed herein, indicated at 810, in the back and in the head of a subject, respectively.

The low-bandwidth data link may operate at a bandwidth of, for example, 100 kbps and may support down-links of on-the-fly stimulation profile updates, down-links of system firmware updates, and up-links of system status and safety data. The high-bandwidth data link may operate at a bandwidth of, for example, 20 Mbps and may support greater than 1,000 channels of local field potential (LFP)/electromyography (EMG) data (18 bit, 1,000 kilo samples per second (kSps)), 55 channels of raw spike data (18 bit, 20 kSps), and 125 channels of compressed spike data (8 bit, 20 kSps).

Increased channels of neural data, particularly spike (AP) data, creates challenges for real-time embedded processing and wireless data transmission. Embodiments of the wireless implants disclosed herein may implement low-power compression algorithms that may reduce data rates in half (16:7) with negligible effects on spike sorting fidelity. This reduction of wireless data bandwidth enables power savings and transmission of 2× more channels than might otherwise be achievable. FIG. 9 illustrates the effect of the compression algorithms on data measurements acquired by embodiments of the wireless implants disclosed herein.

Figure 10:
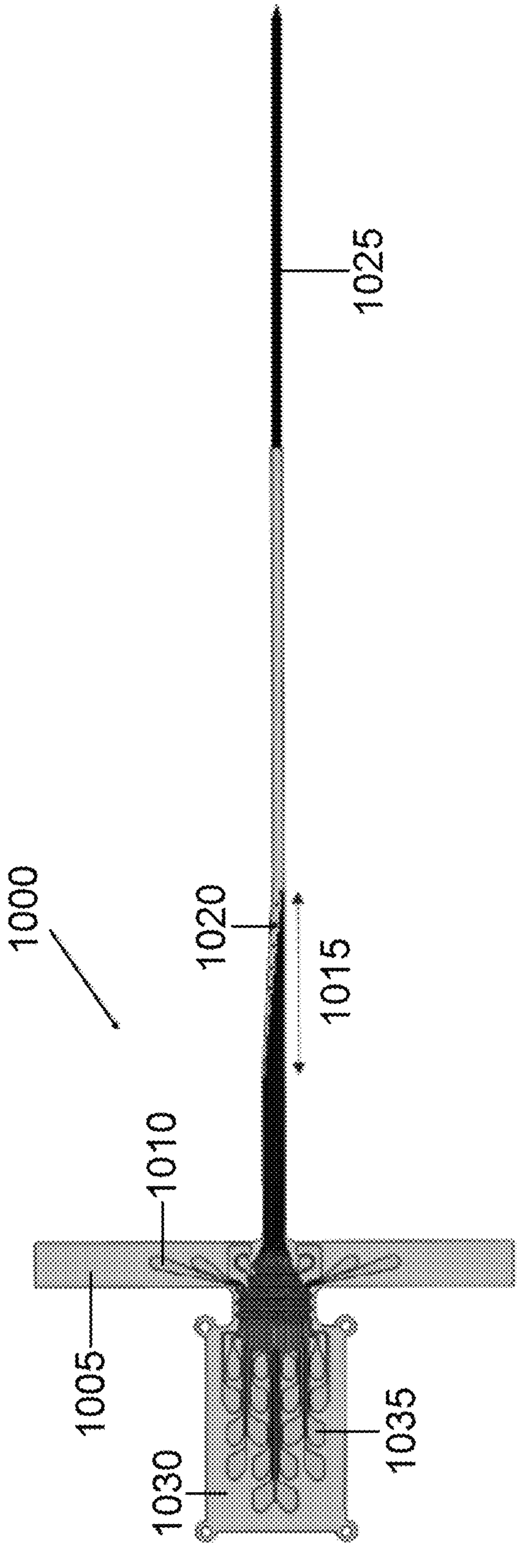
FIG. 10 illustrates an electrode system that may be utilized with examples of wireless implants.

Electrodes that may be electrically connected to embodiments of the wireless implants disclosed herein may be inserted into, for example, muscle tissue or nervous tissue of a subject to monitor the electrical activity of these tissues or apply stimulation to same. One example of an electrode that may be utilized with embodiments of the wireless implants disclosed herein is referred to as a longitudinal intra-fascicular electrode (LIFE) system. The LIFE electrode system formed of platinum and silicone and include fine features which are designed to be implanted within the body of a peripheral nerve of a subject. The LIFE electrode system, illustrated generally at 1000 in FIG. 10, includes a cuff 1005 having six cuff electrodes 1010 for macro recording, stimulation, and proving a secure anchoring point around a nerve. The LIFE electrode system 1000 further includes an inter-fascicular active area 1015 including nine intra-neural electrodes 1020 for micro recording and stimulation for more precise motor control and sensory perception. A needle 1025 at the tip of the electrode system 1000 allows for easy and simplified implantation within individual motor and sensory fascicles for safer and more reliable access to targeted neurons. Bond pads 1035 on a bonding surface 1030 coupled to the cuff 1005 provide electrical contact to each of the cuff electrodes 1010 and intra-neural electrodes 1020 which are in turn electrically connected to electrical contacts 330 or feedthroughs 410 of embodiments of a wireless implant as disclosed herein.

Figure 11A:
FIG. 11A illustrates in act in the electrode system of FIG. 10 being attached to a nerve.
Figure 11B:
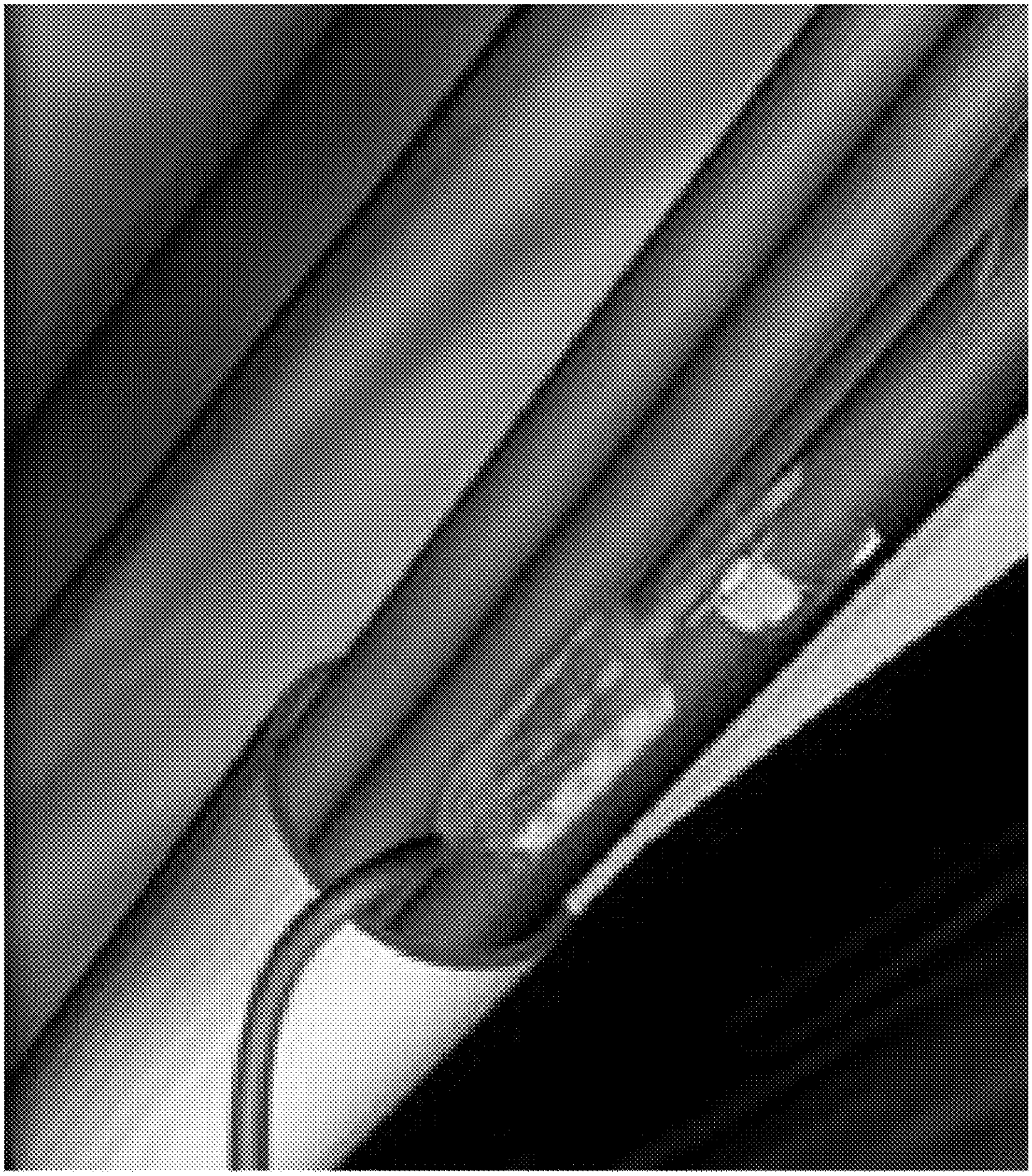
FIG. 11B illustrates another act in the electrode system of FIG. 10 being attached to a nerve.
Figure 11C:
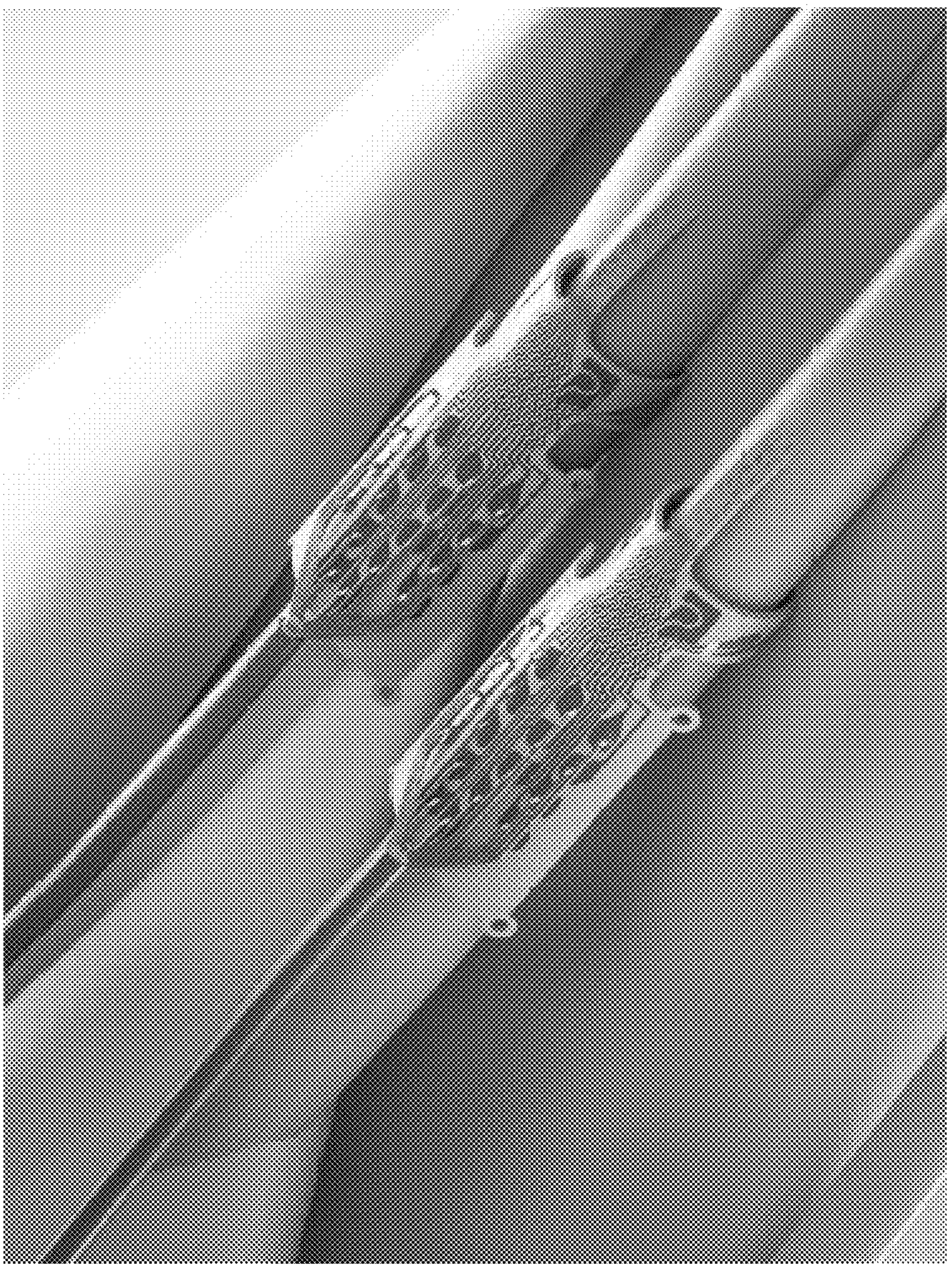
FIG. 11C illustrates the electrode system of FIG. 10 attached to a nerve and having signal wires connected to bond pads of the electrode system.

In use, the LIFE electrode system is threaded into the fibers of the nerves using the suture needle 1025 located at the end of the active sites, as shown in FIG. 11A. Once the electrode system is properly placed, the needle is removed (FIG. 11B). The electrode system is then secured closely to the nerve fibers to form a selective neural interface and the wires for connection to a wireless implant are connected to the bond pads 135 (FIG. 11C).

It should be appreciated that embodiments of the wireless implants disclosed herein are not limited to sending or receiving electrical signals from electrodes. In other embodiments other forms of sensors, for example, blood pressure, blood oxygen, glucose level, insulin level, or other forms of mechanical or chemical sensors may be utilized to provide data to embodiments of the wireless implants. In alternate embodiments, outputs of embodiments of the wireless implants may be utilized to drive a chemical dispenser or drug delivery system or to drive a heating, cooling, or light emitting device or one that applies mechanical force to one or more portions of a body of a subject.

Figure 12:
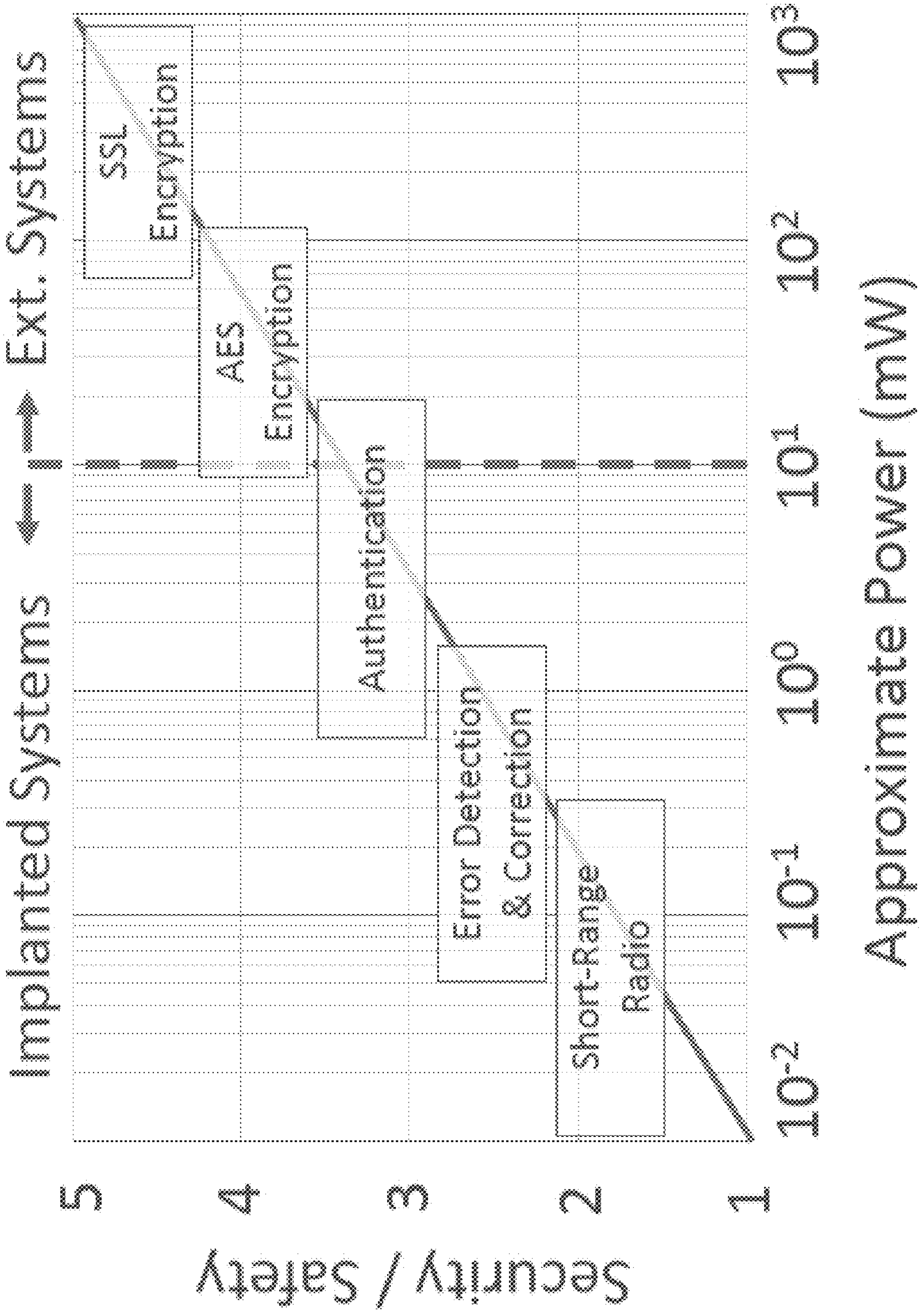
FIG. 12 illustrates a graph showing power consumption associated with different security and safety features of systems including wireless implants.

In some embodiments, wireless implants as disclosed herein may be provided with wireless security measures to prevent hacking. Implantable medical devices are typically more power constrained than external systems and designs of such systems may include a trade-off between power and security. FIG. 12 illustrates a graph showing power consumption associated with different security and safety features. Embodiments of wireless implants disclosed herein may include security algorithms requiring authentication, for example, multi-factor authentication or proximity-based authentication. Such algorithms may be reprogrammable. Confidentiality features of embodiments of wireless implants disclosed herein may include resting data encryption and/or SSL architecture for transit data. Data integrity features of wireless implants disclosed herein may include error detection and automatic repeat request (ARQ). Availability features of embodiments of wireless implants disclosed herein may include an integrated network and short-range radio.

PROPHETIC EXAMPLES

Prophetic Example 1: Restoration of Sensorimotor Function in an Upper Arm Amputee Through a Sensorized Robotic Arm An example application of a wirelessly networked implantable system is to restore sensorimotor function in an upper arm amputee through a sensorized robotic arm. In this example, control of the prosthetic arm could be derived from signals recorded from residual muscle and nerve in the amputated limb. To provide control signals for movement of the prosthetic, muscle activity could be recorded from intramuscular or epimysial electromyography (EMG) electrodes. Control signals for flexion or extension around a joint could be derived from different muscle groups that are involved in similar natural movement, which are often located on opposite sides of the limb. Two implants could be used to record activity from each group—one located near to the extensors and one located near to the flexors. Recorded EMG activity could be processed within each implant. The power of the EMG signals may be estimated using an envelope detection method that rectifies and low-pass filters the raw EMG data. Alternatively, control signals could be derived from motor neurons using cuff or intrafascicular electrodes.

Targeted nerves are typically more proximal than the muscles that they innervate and so the location of an implant that interfaces with nerve would likely be more proximal than implants that interface with muscles. Neural recording requires a wider amplifier bandwidth and higher sampling rate than EMG, and which could be configured via the wireless down-link to an implant. Neural signals could be processed within an implant, which might include threshold detection, action potential sorting, and calculation of spike rates. Depending upon the chosen algorithms, the power to wirelessly transmit the neural signals to the external device may be less than the power to perform the processing within the implant. In such instances, the neural data, which has a greater sampling rate than EMG, may be compressed and transmitted to the external device within an allocated time slot that is proportionally longer in duration than the time slot duration allocated to an implant that is recording EMG. The pre-processed signals could then be aggregated by the external device and further processed to create a movement control signal that is transmitted (wirelessly or via a wired connection) to the prosthetic.

To restore sensory function, both muscle and nerve could be stimulated to create sensory perceptions in response to movement and touch on the sensorized prosthetic limb. To create a perception of limb movement, signals from the prosthetic could be received by the external device, which would then convert the signals to desired stimulation patterns that would be sent to implants that are interfacing with the nerve or muscle that are associated with the intended perception. Natural sensation of limb movement involves both the contraction of some muscles, while others are extended on the opposite side of the joint. To replicate this sensation, stimulation might be provided at multiple locations in the limb through multiple distributed implants. Stimulation patterns might be transmitted from the external device to the implants using the low-bandwidth downlink by sending changes in the frequency or amplitude of stimulation to be provided. In this way, the amount of data required for stimulation can be reduced since not all of the stimulation parameters need to be transmitted for every stimulus. Implants may receive the stimulation information that is addressed to them and conduct further processing to create the full stimulation pattern that is required. The timing and location of stimulation can be coordinated across multiple implants to produce a natural sensation.

Prophetic Example 2: Treating Neuropsychiatric Disorders Through Closed-Loop Neuromodulation in the Brain Another example application of a wirelessly networked implantable system is to treat neuropsychiatric disorders through closed-loop neuromodulation in the brain. In this example, coordinated stimulation may be provided at multiple target locations in the brain in response to estimates of unhealthy neuropsychiatric states derived from aggregated neural activity that is distributed throughout the brain. Neuropsychiatric illness is increasingly understood from a systems neuroscience perspective involving dynamic changes in network activity. For example, neural activity that is predictive of neuropsychiatric state may come from electrocorticographic (ECoG) signals recorded from prefrontal cortex and cingulate cortex as well as multi-unit signals from micro-electrode placed deeper within the striatum. In this example, three implants may be used—one in each area. The implants used for ECoG recordings would have their amplifiers configured for lower bandwidth differential recordings, and the implant used for multi-unit recordings would be configured for higher bandwidth single-ended recordings. Power spectra from ECoG recordings may be calculated within specific frequency bands within the implants and results wirelessly transmitted to the external device. Algorithms for spike thresholding, sorting, and calculation of spike rates may be implemented in the implant configured for multi-unit recordings and transmitted to the external device. This data may be aggregated and processed to detect the neuropsychiatric state, which may be subsequently used to trigger coordinated stimulation on multiple electrodes distributed across all implants. Alternatively, features of the recorded signals may be transmitted directly between the implanted network in the absence of the external device and used to modulate stimulation therapies.

Having thus described several aspects of at least one embodiment, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A system, comprising:

two or more implantable medical devices configured to establish an intra-body wireless communication link between the two or more implantable medical devices while the two or more implantable medical devices are implanted in a body of a patient, to coordinate therapy for the patient through the communication link between the two or more implantable medical devices based on one or more physiological parameters of the patient sensed by at least one of the two or more implantable medical devices, and at least one of the two or more implantable medical devices is configured to be one of placed in one of a plurality of low power modes and brought from the one of the plurality of low power modes into an active mode based upon a signal from another of the two or more implantable medical devices.

2. The system of claim 1, wherein the two or more implantable medical devices are further configured to share data processing load through the communication link between each other.

3. The system of claim 1, further comprising a device external to the body of the patient configured to coordinate therapy for the patient performed by the two or more implantable medical devices.

4. The system of claim 1, further comprising a device external to the body of the patient configured to coordinate monitoring of the one or more physiological parameters of the patient by the two or more implantable medical devices.

5. The system of claim 4, wherein coordinating monitoring of the one or more physiological parameters of the patient includes aggregating data acquired by the two or more implantable medical devices to produce aggregated data regarding the one or more physiological parameters of the patient.

6. The system of claim 5, wherein the device external to the body of the patient is further configured to coordinate therapy for the patient performed by the two or more implantable medical devices based on the aggregated data.

7. The system of claim 5, wherein the device external to the body of the patient is further configured to provide the aggregated data to a diagnostic system distinct from the system.

8. The system of claim 5, wherein the device external to the body of the patient is further configured to provide a recommendation for treatment of the patient based on the aggregated data.

9. The system of claim 1, further comprising a device external to the body of the patient, wherein the two or more implantable medical devices are configured to share data processing load through a wireless communication link with the device external to the body of the patient.

10. The system of claim 1, further comprising a device external to the body of the patient, wherein the system is scalable and includes at least an additional implantable medical device having at least one communication link with the device external to the body of the patient.

11. The system of claim 1, where the system automatically adapts to activation, deactivation, addition, or removal of an implantable medical device from the system to coordinate monitoring and therapy of the patient utilizing each active implantable medical device implanted in the patient.

12. The system of claim 1, further comprising a device external to the body of the patient in configured to communicate with the two or more implantable medical devices via a wireless power supply link, a high-speed data link, and a low-speed data link.

13. The system of claim 12, wherein the high-speed data link is an asymmetrical data link that uplinks data received from sensors in the body of the patient by the two or more implantable medical devices to the device external to the body of the patient.

14. The system of claim 12, wherein the low-speed data link is an asymmetrical data link that downlinks configuration settings from the device external to the body of the patient to the two or more implantable medical devices.

15. The system of claim 12, wherein the low-speed data link comprises signals generated by modulating current passing through the power supply link.

16. The system of claim 12, wherein the low-speed data link and high-speed data link are provided in a single signal.

17. The system of claim 12, wherein the device external to the body of the patient includes a plurality of antennas and is configured to determine which of the two or more implantable medical devices transmitted a signal over one of the high- speed data link or the low-speed data link based on a known location of the two or more implantable medical devices and a timing of receipt of the signal at different antennas in the plurality of antennas.

18. The system of claim 1, further comprising a device external to the body of the patient, wherein the two or more implantable medical devices are configured to communicate with the device external to the body of the patient utilizing a time-division multiplexing protocol.

19. The system of claim 1, further comprising a device external to the body of the patient, wherein each of the two or more implantable medical devices have different addresses that provide for the device external to the body of the patient to communicate separately with each of the two or more implantable medical devices.

20. The system of claim 1, wherein the system is a closed-loop system in which the two or more implantable medical devices are configured to communicate to determine therapy to be applied to the patient in the absence of communication with an external device.

21. The system of claim 1, wherein each of the two or more implantable medical devices have a volume of less than about 4 $cm^3$.

22. The system of claim 1, wherein each of the two or more implantable medical devices includes up to 32 different channels to tissue interfaces configured to one of receive sensor data signals or transmit stimulation signals.

23. The system of claim 22, wherein the operating parameters of the channels are reconfigurable, while the two or more implantable medical devices are implanted in the patient, for each of sensing and stimulation by transmission of a down link control signal to the two or more implantable medical devices.

24. The system of claim 1, wherein the two or more implantable medical devices include communications security algorithms including authentication requirements.

25. The system of claim 24, wherein the two or more implantable medical devices include communications security algorithms further including encryption.

26. The system of claim 1, wherein the two or more implantable medical devices are operable to read signals from nerve tissue of the patient and process the signals to provide outputs to control an electronic device.

27. The system of claim 26, wherein the electronic device includes a prosthetic device of the patient.

28. The system of claim 1, wherein the two or more implantable medical devices are reconfigurable, while the two or more implantable medical devices are implanted in the patient, to operate with mixed monopolar and bipolar stimulation modes by transmission of a down link control signal to the two or more implantable medical devices.

29. The system of claim 1, wherein the two or more implantable medical devices are reconfigurable, while the two or more implantable medical devices are implanted in the patient, to switch between performing differential signal recording and performing single-ended signal recording by transmission of a down link control signal to the two or more implantable medical devices.

30. The system of claim 1, wherein the two or more implantable medical devices are further configured to establish a communication link between each other while implanted in the body of the patient utilizing a wired communication link.

* * * * *